United States Patent
Nieman et al.

(10) Patent No.: US 12,186,309 B2
(45) Date of Patent: Jan. 7, 2025

(54) RNA VIRUS INHIBITOR COMPOUNDS AND USES THEREOF

(71) Applicant: The Governors of the University of Alberta, Edmonton (CA)

(72) Inventors: James A. Nieman, Sherwood Park (CA); M. Joanne Lemieux, Edmonton (CA); D. Lorne Tyrrell, Edmonton (CA); Mostofa Hena, Edmonton (CA); Appan Srinivas Kandadai, Edmonton (CA); Alexandr Belovodskiy, Edmonton (CA); Michael A. Joyce, Edmonton (CA); Elena Arutyunova, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 17/950,785

(22) Filed: Sep. 22, 2022

(65) Prior Publication Data

US 2023/0108588 A1 Apr. 6, 2023

Related U.S. Application Data

(60) Provisional application No. 63/350,542, filed on Jun. 9, 2022, provisional application No. 63/248,916, filed on Sep. 27, 2021.

(51) Int. Cl.
*A61K 31/454* (2006.01)
*A61P 31/14* (2006.01)

(52) U.S. Cl.
CPC ............ *A61K 31/454* (2013.01); *A61P 31/14* (2018.01)

(58) Field of Classification Search
CPC .............................. A61K 31/454; A61P 31/14
See application file for complete search history.

(56) References Cited

U.S. PATENT DOCUMENTS

2022/0204476 A1 6/2022 Nieman et al.

FOREIGN PATENT DOCUMENTS

| WO | 2021250648 | 12/2021 |
| WO | 2021252644 | 12/2021 |

*Primary Examiner* — San Ming R Hui
(74) *Attorney, Agent, or Firm* — Rudy J. Ng; Bozicevic, Field & Francis LLP

(57) ABSTRACT

The present disclosure provides compounds and methods for inhibiting a virus infection, such as a Baltimore Group IV RNA virus infection. Aspects of the present disclosure also include methods of treating a Baltimore Group IV RNA virus infection in a subject. The present disclosure also provides pharmaceutical compositions related to the same.

24 Claims, 1 Drawing Sheet

RNA VIRUS INHIBITOR COMPOUNDS AND USES THEREOF

CROSS-REFERENCE TO RELATED APPLICATIONS

This application claims the benefit of U.S. Provisional Application No. 63/248,916, filed Sep. 27, 2021, and U.S. Provisional Application No. 63/350,542, filed Jun. 9, 2022, the disclosures of which are incorporated herein by reference.

INTRODUCTION

RNA viruses have genomes made of RNA. RNA viruses may be categorized based on their genetic material by the Baltimore classification strategy. The groups include, for example, double-stranded RNA (dsRNA) viruses (Group III), positive sense single-stranded RNA viruses (+ssRNA) viruses (Group IV), and negative sense single-stranded NRA (-ssRNA) viruses (Group V). Single-stranded RNA (ssRNA) viruses cause many diseases in wildlife, domestic animals and humans. These viruses are genetically and antigenically diverse, exhibiting broad tissue tropisms and a wide pathogenic potential. The incubation periods of some of the most pathogenic viruses, e.g. the caliciviruses, are very short. Viral replication and expression of virulence factors may overwhelm early defense mechanisms (Xu 1991) and cause acute and severe symptoms.

Group IV RNA viruses contain a single strand of viral mRNA (also known as a positive/plus strand of genomic RNA). Positive sense RNA can be translated directly into protein, without a DNA intermediate and without creating a complementary RNA strand. The positive strand RNA genome is independently infectious, for most Group IV viruses. This means that in the absence of a capsid, envelope, or enclosed proteins, the RNA molecule, when inserted into a cell, is capable of using host cell machinery to construct additional viruses. Six subclasses of the Group IV single-stranded positive-sense RNA viruses include: Picornaviridae, Togaviridae, Coronaviridae, Hepeviridae, Caliciviridae, Flaviviridae, and Astroviridae (Berman (2012) *Taxonomic Guide to Infectious Diseases*. 237-246.).

Coronaviruses are a group of enveloped positive-sense single-stranded RNA viruses that are members of the Coronaviridae family, which are members of Group IV viruses. Since the turn of the millennium, three closely related coronaviruses have infected humans and spread internationally: the 2003 epidemic of Severe Acute Respirator Syndrome (SARS), 2012 Middle East respiratory syndrome (MERS) outbreak and the current Coronavirus Disease 2019 (COVID-19) pandemic. In each instance, these coronaviruses are thought to have originated from an animal reservoir and then 'jumped' to humans either directly or through an intermediate species. COVID-19 is caused by the Severe Acute Respiratory Syndrome Coronavirus 2 (SARS-CoV-2 or SARS2).

Noroviruses are a group of non-enveloped, positive-sense single-stranded RNA viruses that are members of the Caliciviridae family, which are members of Group IV viruses. Noroviruses is the most common cause of gastroenteritis and cases result in approximately 200,000 deaths globally per year.

Rhinoviruses have single-stranded positive sense RNA genomes and are not enveloped. They are members of the Picornaviridae family, which are members of Group IV viruses. Rhinoviruses are a predominant cause of the common cold. Rhinoviruses belong to the genus Enterovirus.

Coxsackieviruses are non-enveloped, positive-sense single-stranded RNA viruses that are members of the Picornaviridae family, which are members of Group IV viruses. Coxsackieviruses cause a variety of infections and are among the leading cause of aseptic meningitis. Coxsackieviruses belong to the genus Enterovirus.

SUMMARY

The present disclosure provides compounds and methods for inhibiting a virus infection, such as a Baltimore Group IV RNA virus infection. Aspects of the present disclosure also include methods of treating a virus infection in a subject. The present disclosure also provides pharmaceutical compositions related to the same.

Aspects of the present disclosure include a compound of formula (I):

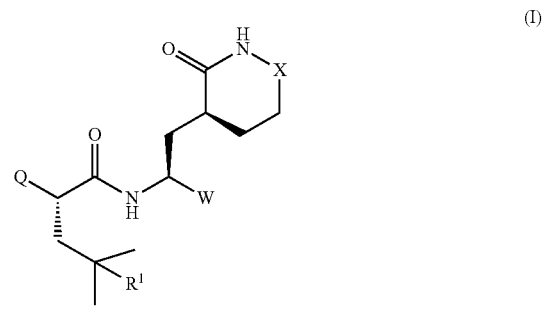

wherein:

W is selected from —CN and —C(=O)CH$_2$OC(=O)—R$^2$;

R$^1$ is selected from —H, —F and —CH$_3$;

R$^2$ is selected from

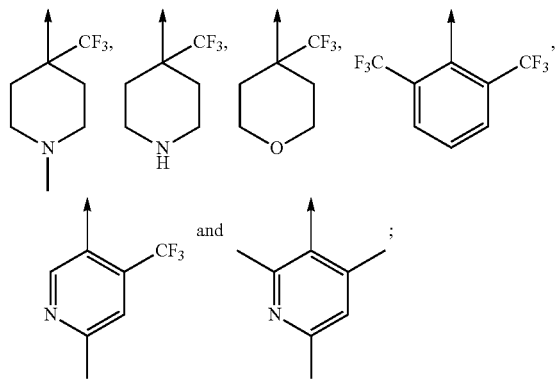

X is selected from —CH$_2$—, —C(CH$_3$)H—, —C(CH$_3$)$_2$—, and

or is absent;
Q is selected from

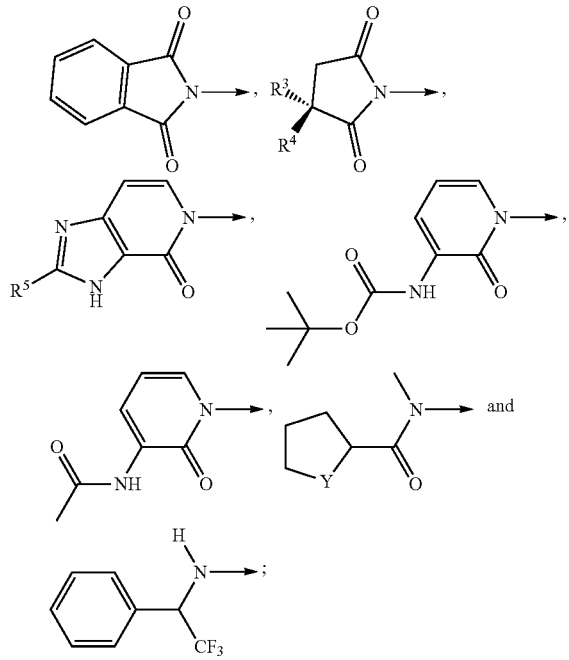

R³ and R⁴ are independently selected from —H, —CH₃ and phenyl, or together with the carbon they are attached to form a $C_3$-$C_6$ carbocycle;

R⁵ is selected from —CH₃, —CHF₂, —CF₃, —CH₂CH₃, —CH(CH₃)₂, —C(CH₃)₃, cyclopropyl and pyridyl; and Y is selected from —CH₂—, —CH₂CH₂—, —O—, —CH₂O—, —NH—, —CH₂NH—, and —C(=O)NH—;

or a pharmaceutically acceptable salt, solvate, or hydrate thereof.

In some embodiments, W is CN. In some embodiments, W is —C(=O)CH₂O—R².

In some embodiments, R¹ is selected from —H and —CH₃. In some embodiments, R¹ is —H.

In some embodiments, X is select from —C(CH₃)H—, —C(CH₃)₂—, and

In some embodiments, X is —CH₂—.

In some embodiments, R² is selected from

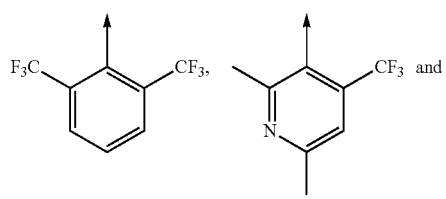

In some embodiments, R² is

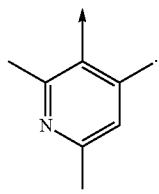

In some embodiments, R² is

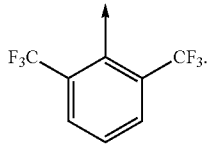

In some embodiments, R² is

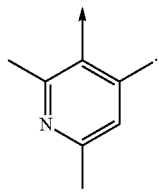

In some embodiments, Q is selected from

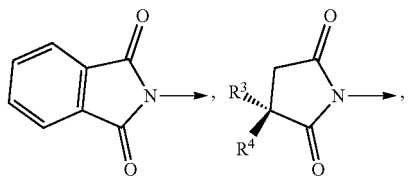

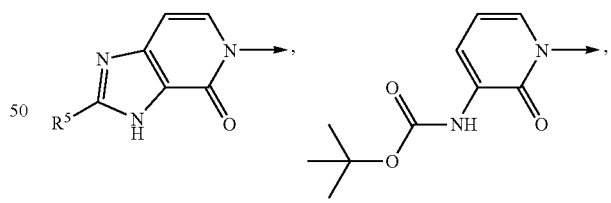

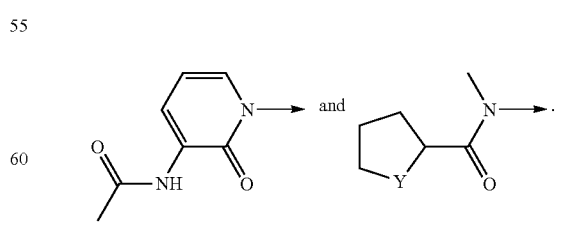

In some embodiments, Y is selected from —CH₂—, —O—, and —NH—.

In some embodiments, Q is selected from

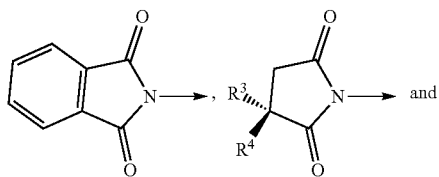

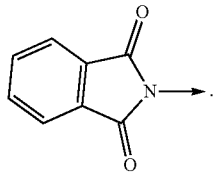 [SMILES: O=C1NC(=O)c2ccccc21]

In some embodiments, Q is

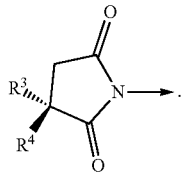

In some embodiments, Q is

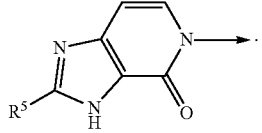

In some embodiments, Q is

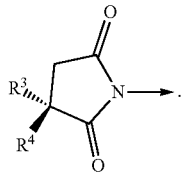

In some embodiments, $R^3$ and $R^4$ are independently selected from —H, —$CH_3$ and phenyl. In some embodiments, $R^5$ is selected from —$CH_3$, —$CHF_2$, —$CH_2CH_3$, and —$CH(CH_3)_2$. In some embodiments, $R^5$ is —$CH_3$. In some embodiments, $R^5$ is —$CHF_2$.

In some embodiments, the compound is of formula (Ia):

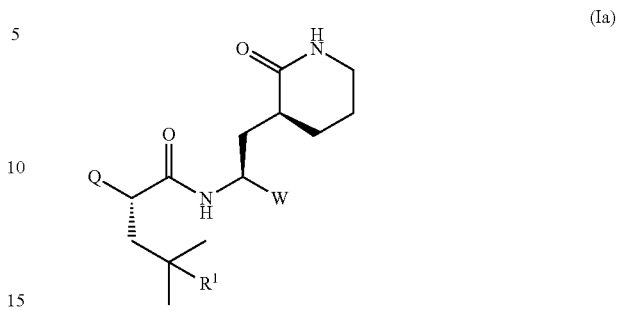

(Ia)

wherein:
W is selected from —CN and —C(=O)$CH_2$OC(=O)—$R^2$;
$R^1$ is selected from —H, —F and —$CH_3$;
$R^2$ is selected from

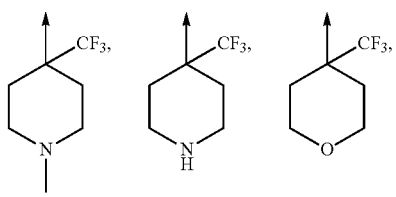

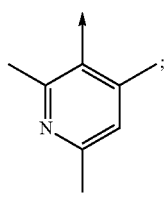

Q is selected from

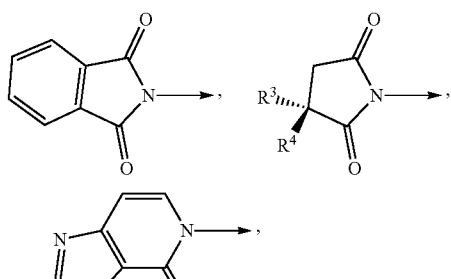

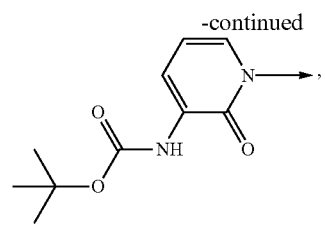

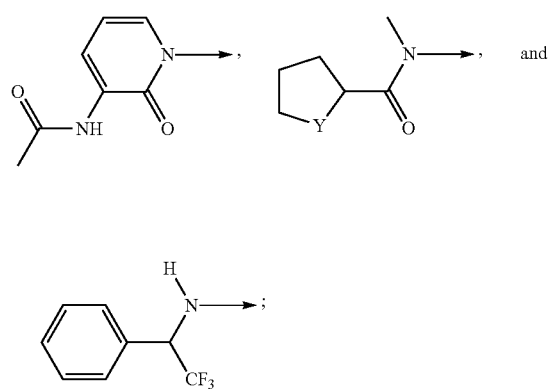

R³ and R⁴ are independently selected from —H, —CH₃ and phenyl, or together with the carbon they are attached to form a C₃-C₆ carbocycle;

R⁵ is selected from —CH₃, —CHF₂, —CF₃, —CH₂CH₃, —CH(CH₃)₂, —C(CH₃)₃, cyclopropyl and pyridyl; and Y is selected from —CH₂—, —CH₂CH₂—, —O—, —CH₂O—, —NH—, —CH₂NH—, and —C(=O)NH—;

or a pharmaceutically acceptable salt, solvate, or hydrate thereof.

In some embodiments, the compound is selected from the following structures:

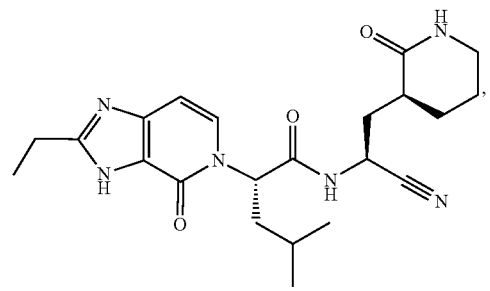

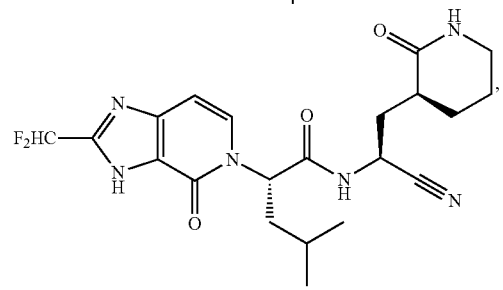

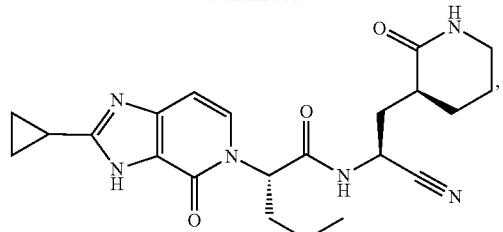

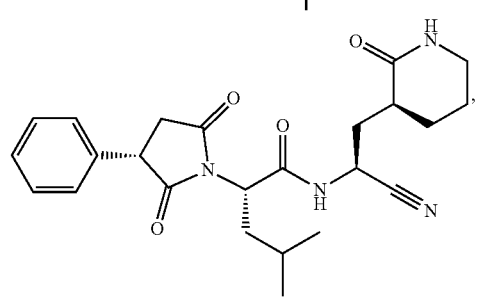

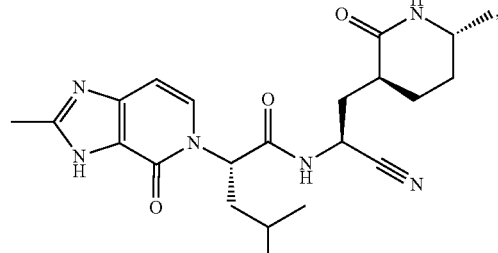

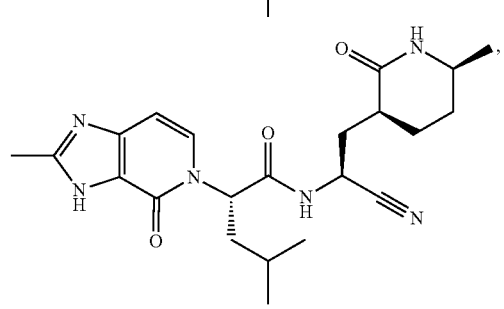

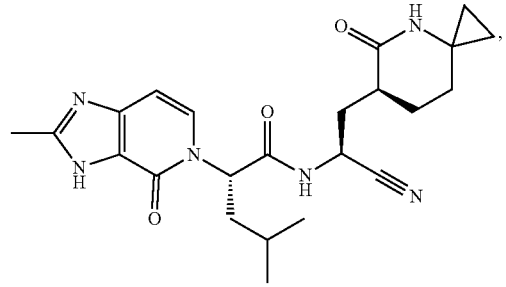

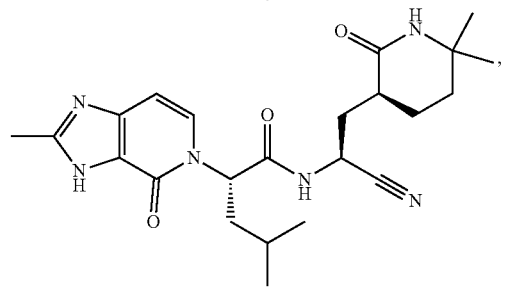

-continued
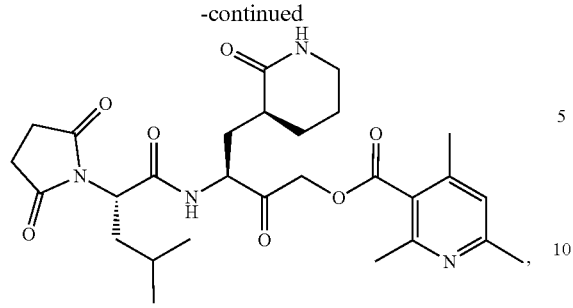
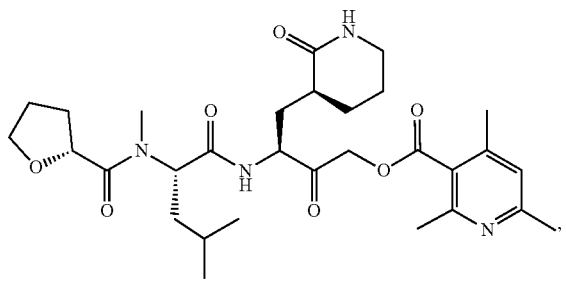
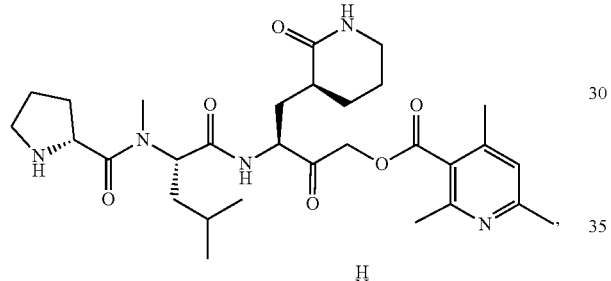
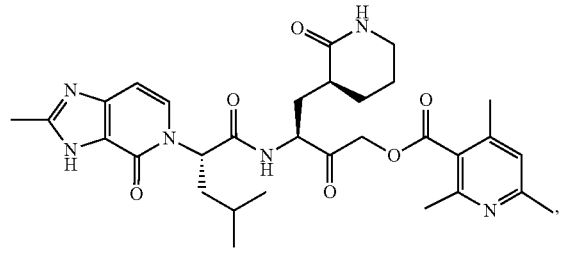
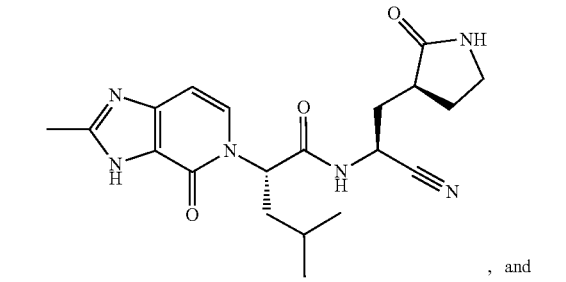
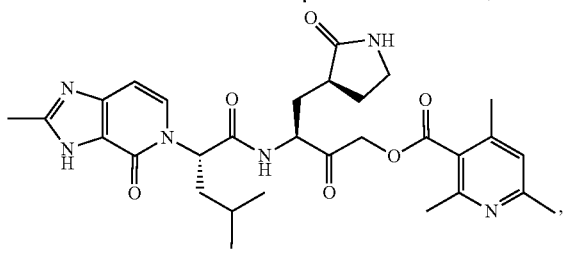
, and
In some embodiments, the compound is selected from the following structures:
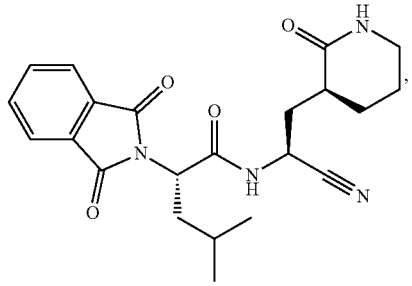
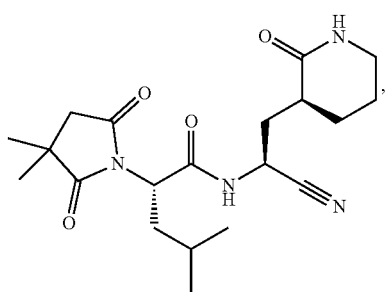
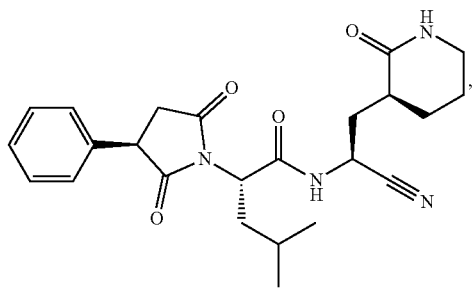
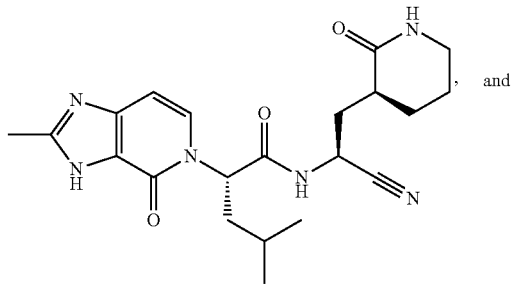
, and
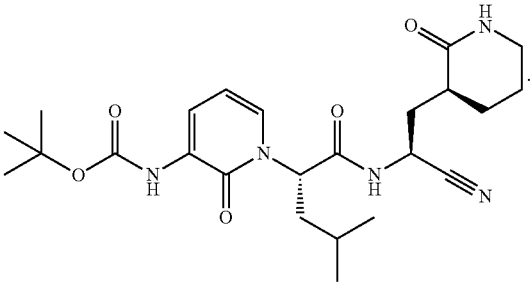

Aspects of the present disclosure include a compound of formula (II):

[Structure of Formula (II)]

wherein:

$R^6$ is selected from —CH$_3$ and —CHF$_2$;

each $R^7$ is independently selected from —H, -D and —CH$_3$, or together two $R^7$ and the carbon they are attached to form a cyclopropyl group; and Z is selected from —CH$_2$CH$_2$CH$_2$— and —C(CH$_3$)$_2$—;

or a pharmaceutically acceptable salt, solvate, or hydrate thereof.

In some embodiments, the compound is selected from the following structures:

[Chemical structures]

Aspects of the present disclosure include a method of inhibiting a Baltimore Group IV RNA virus in a cell infected with a Baltimore Group IV RNA virus, the method comprising contacting the cell with a compound according to the present disclosure.

In some embodiments, the Baltimore Group IV RNA virus is selected from picornavirus, norovirus, and coronavirus.

In some embodiments, the Baltimore Group IV RNA virus is selected from enterovirus, rhinovirus, coxsackie virus, norovirus and coronavirus.

In some embodiments, the Baltimore Group IV RNA virus is coronavirus.

In some embodiments, the coronavirus is one that causes disease in mammals. In some embodiments, the coronavirus causes disease in companion animals or livestock. In some embodiments, the coronavirus is a feline coronavirus. In some embodiments, the coronavirus is feline infectious peritonitis. In some embodiments, the coronavirus is a human coronavirus.

In some embodiments, the coronavirus is selected from Severe Acute Respiratory Syndrome coronavirus 2 (SARS-CoV-2), Severe Acute Respiratory syndrome coronavirus 1 (SARS-CoV-1) and Middle Eastern Respiratory syndrome-related coronavirus (MERS-CoV).

Aspects of the present disclosure include a method of treating a Baltimore Group IV RNA virus infection in a mammal, the method comprising administering to the mammal an effective amount of a compound according to the present disclosure.

In some embodiments, the mammal is selected from a companion animal and livestock. In some embodiments, the mammal is a feline. In some embodiments, the mammal is a human.

In some embodiments, the Baltimore Group IV RNA virus is selected enterovirus, rhinovirus, coxsackie virus, norovirus and coronavirus.

In some embodiments, the Baltimore Group IV RNA virus is selected from norovirus, and coronavirus.

In some embodiments, the Baltimore Group IV RNA virus is human norovirus.

In some embodiments, the Baltimore Group IV RNA virus is a coronavirus that causes disease in mammals.

In some embodiments, the coronavirus is a feline coronavirus. In some embodiments, the feline coronavirus is feline infectious peritonitis.

In some embodiments, the coronavirus is a human coronavirus. In some embodiments, the human coronavirus is selected from Severe Acute Respiratory Syndrome coronavirus 2 (SARS-CoV-2), Severe Acute Respiratory syndrome coronavirus 1 (SARS-CoV-1) and Middle Eastern Respiratory syndrome-related coronavirus (MERS-CoV).

DEFINITIONS

Figures 1A, 1B, 1C:
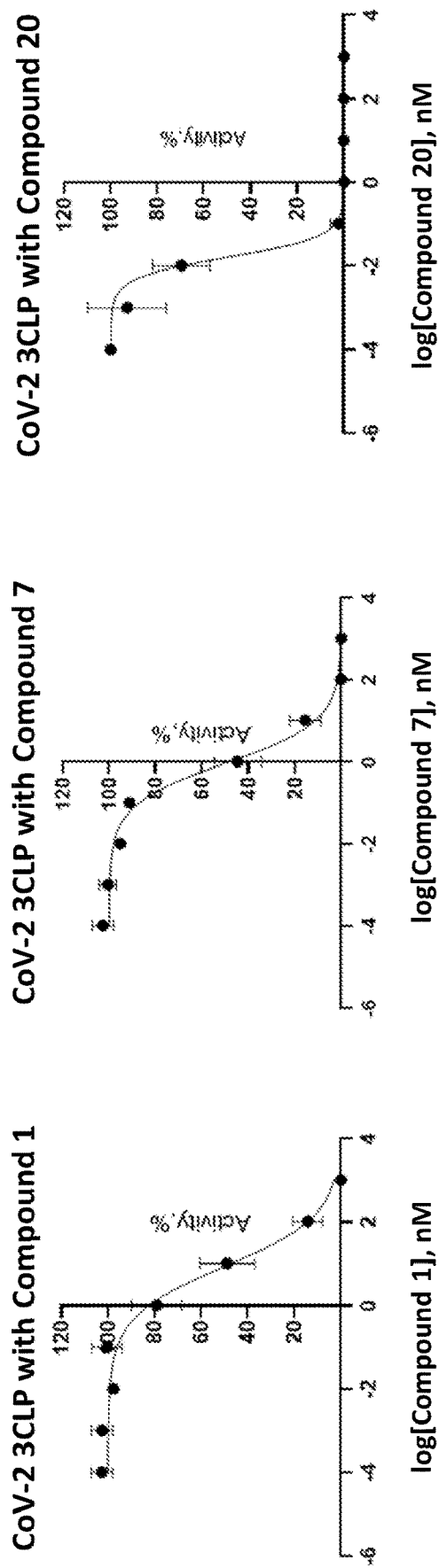
FIGS. 1A to 1C show exemplary concentration response curves for compounds screened for SARS-CoV-2 3CLP inhibition using a Fluorescence resonance energy transfer (FRET) assay.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like, where R$^{10}$ is chosen from chosen from hydrogen, optionally substituted alkyl, cycloalkyl, alkenyl, cycloalkenyl, alkynyl, aryl, heteroaryl and heterocyclic. This term includes, by way of example, methylene (—CH$_2$—), ethylene (—CH$_2$CH$_2$—), n-propylene (—CH$_2$CH$_2$CH$_2$—), iso-propylene (—CH$_2$CH($CH_3$)—), (—C($CH_3$)$_2$CH$_2$CH$_2$—), (—C($CH_3$)$_2$CH$_2$C(O)—), (—C($CH_3$)$_2$CH$_2$C(O)NH—), (—CH($CH_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NR$^d$C(O)OR$^d$ where each R$^d$ is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkenyl, cycloalkenyl, substituted cycloalkenyl, aryl, substituted aryl, heteroaryl, substituted heteroaryl, heterocyclic, and substituted heterocyclic are as defined herein.

"Sulfonylamino" refers to the group —NR$^{21}$SO$_2$R$^{22}$, wherein R$^{21}$ and R$^{22}$ independently are selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacylamino, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NR'''R''' where each R''' is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Carbocycle" refers to non-aromatic or aromatic cyclic groups, such as cycloalkyl, cycloalkenyl, cycloalkynyl, and aryl groups as defined herein. A carbocycle group may be unsubstituted or substituted as defined herein.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, heterocyclyl, aryl, or heteroaryl, provided that the point of attachment is through the non-aromatic ring. Fused ring systems include compounds where two rings share two adjacent atoms. In fused heterocycle systems one or both of the two fused rings can be heterocyclyl. In certain embodiments, the nitrogen and/or sulfur atom(s) of the heterocyclic group are optionally oxidized to provide for the N-oxide, —S(O)—, or —SO$_2$— moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, 1,2,3,4-tetrahydroquinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, 3,4-dihydro-1,4-benzoxazine, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O—)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$_2^+$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O—)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

By "treating" or "treatment" is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the subject no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state or prophylactic treatment of a subject; (ii) inhibition, that is, arresting the development or further development of clinical symptoms, e.g., mitigating or completely inhibiting an active disease; and/or (iii) relief, that is, causing the regression of clinical symptoms or alleviating one or more symptoms of the disease or medical condition in the subject.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

As used herein, the term "chronic administration" refers to repeated administration of a compound to a subject. In such treatment, the compound can be administered at least once a week, such as at least once a day, or at least twice or three times a day for a period of at least one month, such as for example five months or more.

As used herein, the term "cysteine protease" refers to a protease having a nucleophilic thiol group in the active site. Cysteine proteases from different organisms can have significantly different cleavage sites. In many RNA class IV viruses, such as coronaviruses, rhinovirus and noroviruses, a well-conserved consensus sequence for the 3-chymotrypsin protease (3CP) and 3-chymotrypsin-like protease (3CLP) are observed. For these viruses, this is the main protease (also known as Mpro) responsible for cleaving the polyprotein generated from translation of the viral genome, which liberates the active viral proteins that are critical for viral replication. As this is not a host protease responsible for other critical functions, producing drugs that are highly selective for this viral protease will allow viral replication to be stopped and minimize toxicity for the host. To obtain sufficient inhibition of the protease activity and selectivity over other protease classes, the catalytic mechanism must also be considered in inhibitor design. For cysteine proteases, forming a covalent bond to the catalytic sulfur will ablate activity as it is vital to the cleavage mechanism; however, in some instances, excessive reactivity of the electrophile will also react with serine proteases, other cysteine proteases and other thiols resulting in toxicity. A moiety that forms the covalent bond to the sulfur in the inhibitor is termed the warhead.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compounds and methods for inhibiting a virus infection, such as a Baltimore Group IV RNA virus infection. Aspects of the present disclosure also include methods of treating a virus infection in a subject. The present disclosure also provides pharmaceutical compositions related to the same.

Compounds

Formula (I)

In certain embodiments, compounds of the present disclosure include a compound of formula (I):

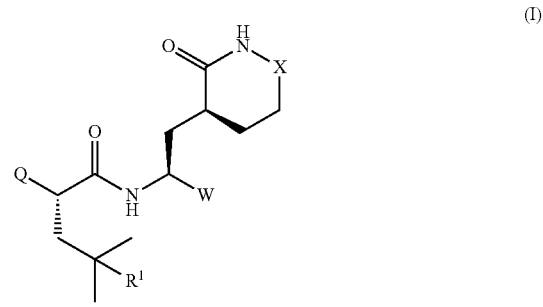

wherein:
W is selected from —CN and —C(=O)CH$_2$OC(=O)—R$^2$;
R$^1$ is selected from —H, —F and —CH$_3$;
R$^2$ is selected from

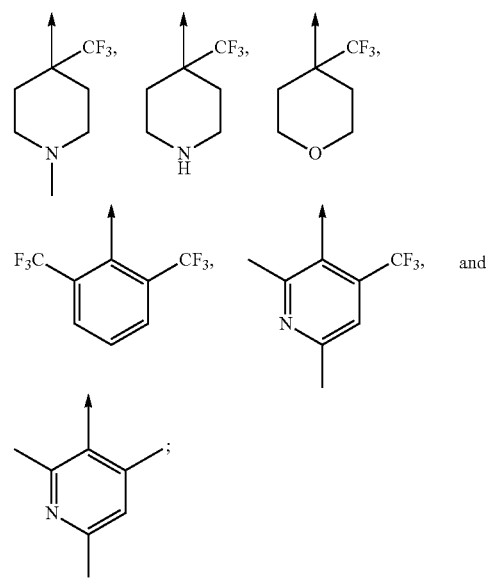

X is selected from —CH$_2$—, —C(CH$_3$)H—, —C(CH$_3$)$_2$—, and

or is absent;
Q is selected from

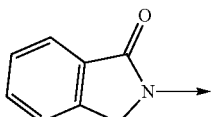 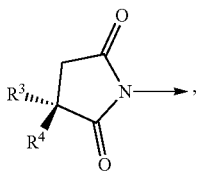

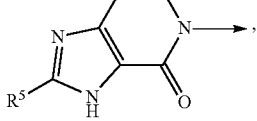

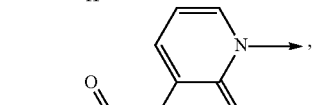

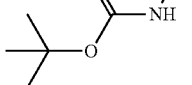

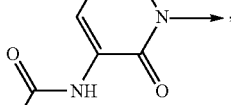

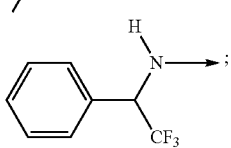

R$^3$ and R$^4$ are independently selected from —H, —CH$_3$ and phenyl, or together with the carbon they are attached to form a C$_3$-C$_6$ carbocycle;
R$^5$ is selected from —CH$_3$, —CHF$_2$, —CF$_3$, —CH$_2$CH$_3$, —CH(CH$_3$)$_2$, —C(CH$_3$)$_3$, cyclopropyl and pyridyl; and
Y is selected from —CH$_2$—, —CH$_2$CH$_2$—, —O—, —CH$_2$O—, —NH—, —CH$_2$NH—, and —C(=O)NH—;
or a pharmaceutically acceptable salt, solvate, or hydrate thereof.

In some embodiments, W is CN. In some embodiments, W is —C(=O)CH$_2$O—R$^2$.

In some embodiments, R$^1$ is selected from —H and —CH$_3$. In some embodiments, R$^1$ is —H.

In some embodiments, X is select from —C(CH$_3$)H—, —C(CH$_3$)$_2$—, and

In some embodiments, X is —CH$_2$—.

In some embodiments, R$^2$ is selected from

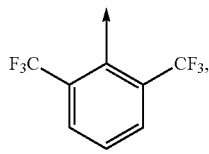 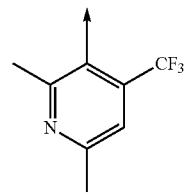 and

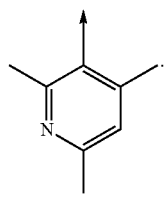

In some embodiments, R$^2$ is

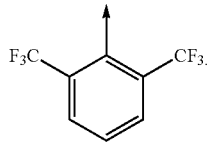

In some embodiments, R$^2$ is

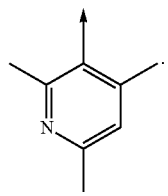

In some embodiments, Q is selected from

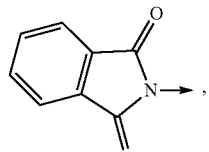 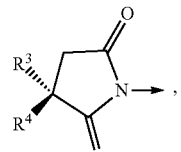

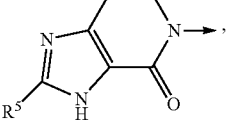 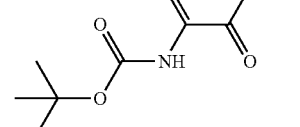

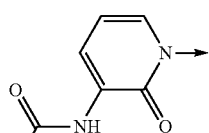 and 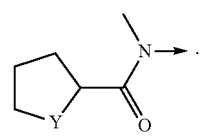

In some embodiments, Y is selected from —CH$_2$—, —O—, and —NH—.

In some embodiments, Q is selected from

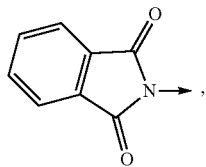 , 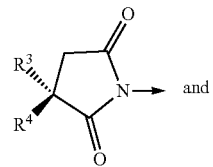 and

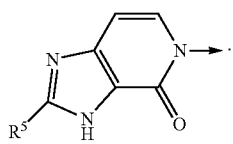

In some embodiments, Q is

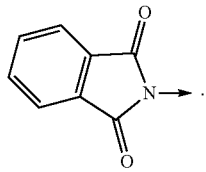

In some embodiments, Q is

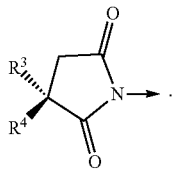

In some embodiments, Q is

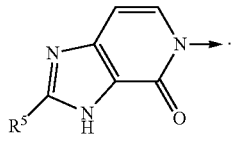

In some embodiments, $R^3$ and $R^4$ are independently selected from is selected from —H, —$CH_3$ and phenyl. In some embodiments, $R^5$ is selected from —$CH_3$, —$CHF_2$, —$CH_2CH_3$, and —$CH(CH_3)_2$. In some embodiments, $R^5$ is —$CH_3$. In some embodiments, $R^5$ is —$CHF_2$.

Formula (Ia)

In certain embodiments of the compound of formula (I), X is —$CH_2$—. Accordingly, In certain embodiments, compounds of the present disclosure include a compound of formula (Ia):

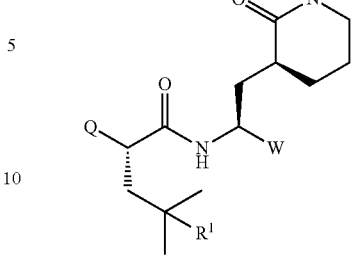

(Ia)

wherein:

W is selected from —CN and —C(=O)CH$_2$OC(=O)—R$^2$;

R$^t$ is selected from —H, —F and —CH$_3$;

R$^2$ is selected from

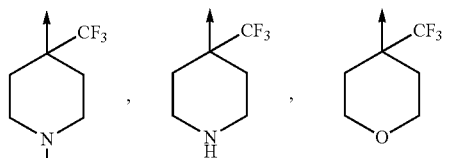

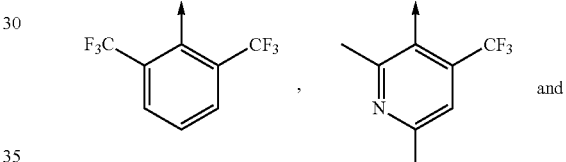 and

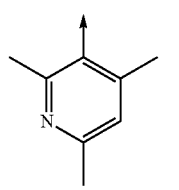 ;

Q is selected from

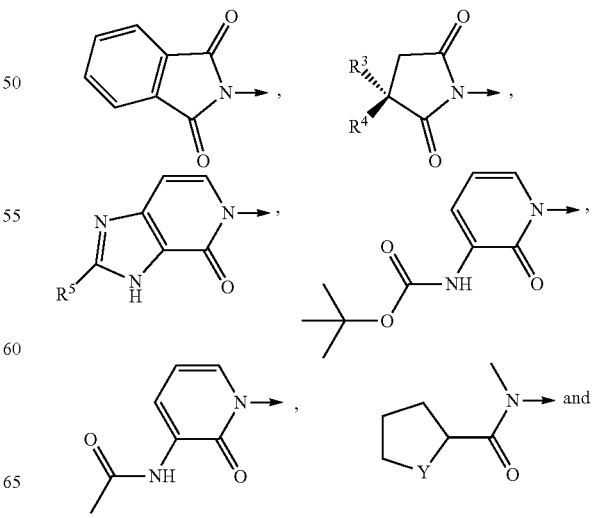

-continued

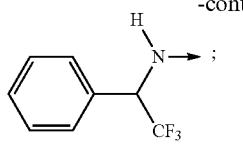

$R^3$ and $R^4$ are independently selected from —H, —CH$_3$ and phenyl, or together with the carbon they are attached to form a C$_3$-C$_6$ carbocycle;

$R^5$ is selected from —CH$_3$, —CHF$_2$, —CF$_3$, —CH$_2$CH$_3$, —CH(CH$_3$)$_2$, —C(CH$_3$)$_3$, cyclopropyl and pyridyl; and Y is selected from —CH$_2$—, —CH$_2$CH$_2$—, —O—, —CH$_2$O—, —NH—, —CH$_2$NH—, and —C(=O)NH—;

or a pharmaceutically acceptable salt, solvate, or hydrate thereof.

Formula (II)

In certain embodiments, the compound is a compound of formula (II):

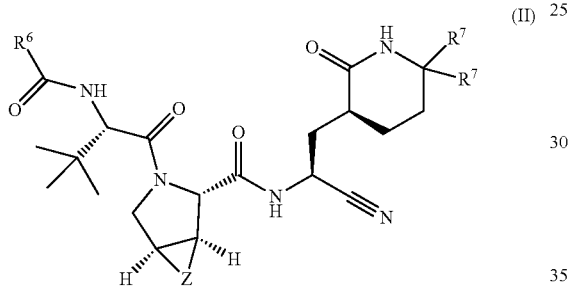

(II)

wherein:
$R^6$ is selected from —CH$_3$ and —CHF$_2$;
each $R^7$ is independently selected from —H, -D and —CH$_3$, or together two $R^7$ and the carbon they are attached to form a cyclopropyl group; and
Z is selected from —CH$_2$CH$_2$CH$_2$— and —C(CH$_3$)$_2$—;
or a pharmaceutically acceptable salt, solvate, or hydrate thereof.

In certain embodiments, compounds of Formula (I) or Formula (Ia) the present disclosure (e.g., compounds that find use in the methods of the present disclosure) include compounds selected from:

Compound 1

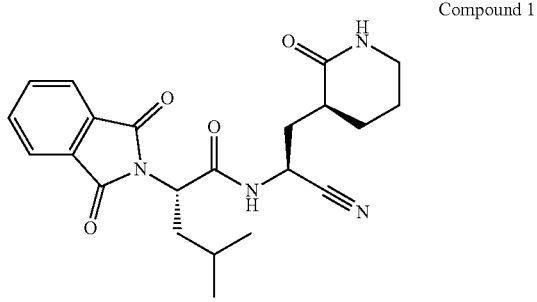 [SMILES: CC(C)C[C@@H](C(=O)N[C@H](C#N)C[C@@H]1CCCNC1=O)N1C(=O)c2ccccc2C1=O]

(2S)—N-{(1S)-1-cyano-2-[(3S)-2-oxopiperidin-3-yl]ethyl}-2-(1,3-dioxo-1,3-dihydro-2H-isoindol-2-yl)-4-methylpentanamide;

Compound 2

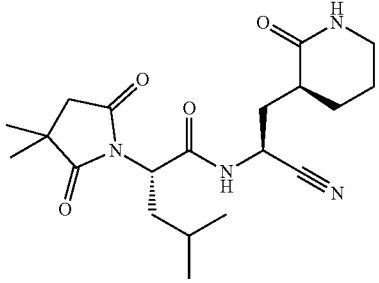

(2S)—N-{(1S)-1-cyano-2-[(3S)-2-oxopiperidin-3-yl]ethyl}-2-(3,3-dimethyl-2,5-dioxopyrrolidin-1-yl)-4-methylpentanamide;

Compound 3

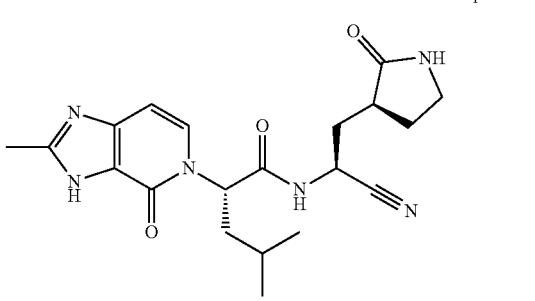

(2S)—N-{(1S)-1-cyano-2-[(3S)-2-oxopyrrolidin-3-yl]ethyl}-4-methyl-2-(2-methyl-4-oxo-3,4-dihydro-5H-imidazo[4,5-c]pyridin-5-yl)pentanamide;

Compound 4

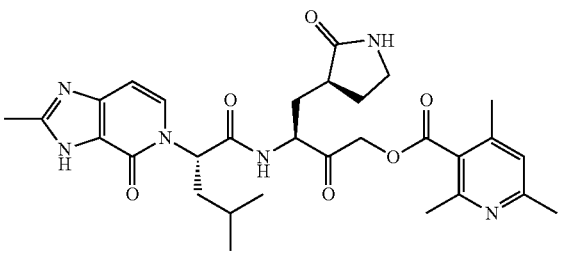

(3S)-3-{[(2S)-4-methyl-2-(2-methyl-4-oxo-3,4-dihydro-5H-imidazo[4,5-c]pyridin-5-yl)pentanoyl]amino}-2-oxo-4-[(3S)-2-oxopyrrolidin-3-yl]butyl 2,4,6-trimethylpyridine-3-carboxylate;

Compound 5

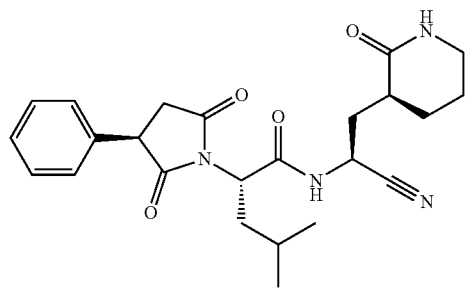

(2S)—N-{(1S)-1-cyano-2-[(3S)-2-oxopiperidin-3-yl]
ethyl}-2-[(3R)-2,5-dioxo-3-phenylpyrrolidin-1-yl]-4-
methylpentanamide;

Compound 8

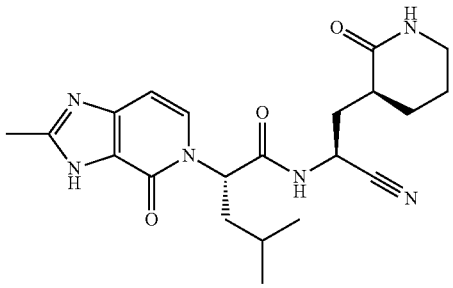

(2S)—N-{(1S)-1-cyano-2-[(3S)-2-oxopiperidin-3-yl]
ethyl}-4-methyl-2-(2-methyl-4-oxo-3,4-dihydro-5H-imi-
dazo[4,5-c]pyridin-5-yl)pentanamide;

Compound 6

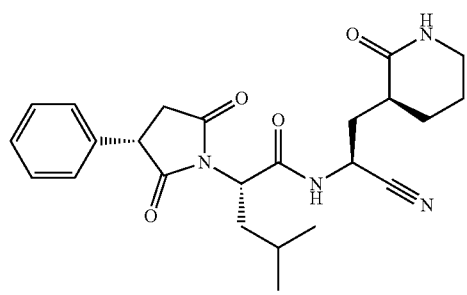

(2S)—N-{(1S)-1-cyano-2-[(3S)-2-oxopiperidin-3-yl]
ethyl}-2-[(3S)-2,5-dioxo-3-phenylpyrrolidin-1-yl]-4-
methylpentanamide;

Compound 9

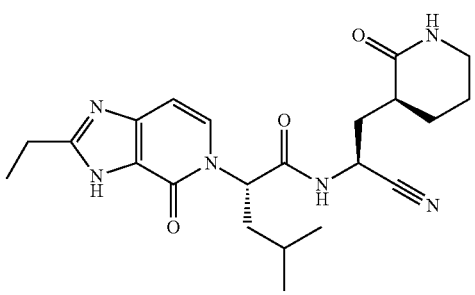

(2S)—N-{(1S)-1-cyano-2-[(3S)-2-oxopiperidin-3-yl]
ethyl}-2-(2-ethyl-4-oxo-3,4-dihydro-5H-imidazo[4,5-c]
pyridin-5-yl)-4-methylpentanamide;

Compound 7

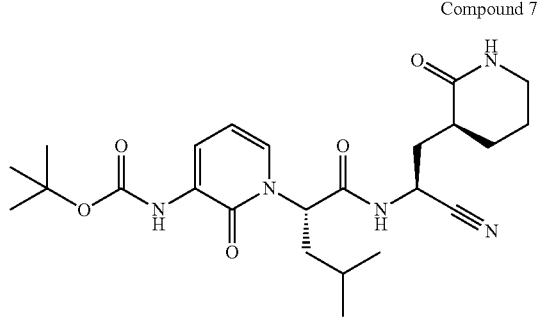 [SMILES: CC(C)C[C@@H](C(=O)N[C@H](C#N)C[C@@H]1CCCNC1=O)n1cccc(NC(=O)OC(C)(C)C)c1=O]

tert-butyl {1-[(2S)-1-({(1S)-1-cyano-2-[(3S)-2-oxopiperi-
din-3-yl]ethyl}amino)-4-methyl-1-oxopentan-2-yl]-2-
oxo-1,2-dihydropyridin-3-yl}carbamate;

Compound 10

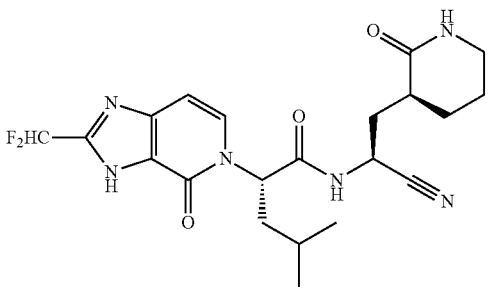

(2S)—N-{(1S)-1-cyano-2-[(3S)-2-oxopiperidin-3-yl]
ethyl}-2-[2-(difluoromethyl)-4-oxo-3,4-dihydro-5H-imi-
dazo[4,5-c]pyridin-5-yl]-4-methylpentanamide;

Compound 11

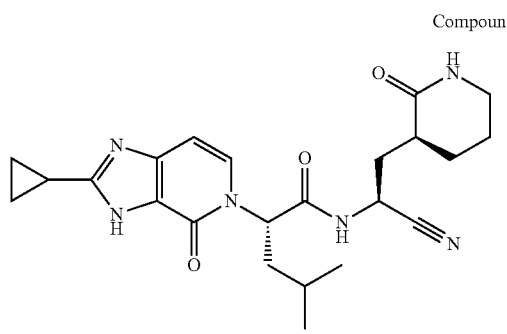

(2S)—N-{(1S)-1-cyano-2-[(3S)-2-oxopiperidin-3-yl]
ethyl}-2-(2-cyclopropyl-4-oxo-3,4-dihydro-5H-imidazo
[4,5-c]pyridin-5-yl)-4-methylpentanamide;

Compound 14

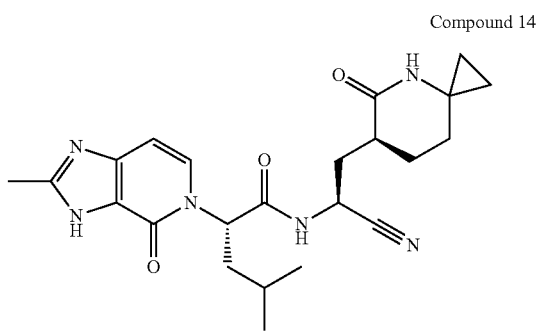 [SMILES: Cc1nc2ccn([C@@H](CC(C)C)C(=O)N[C@H](C#N)C[C@@H]3CCC4(CC4)NC3=O)c(=O)c2[nH]1]

(2S)—N-{(1S)-1-cyano-2-[(6S)-5-oxo-4-azaspiro[2.5]oc-
tan-6-yl]ethyl}-4-methyl-2-(2-methyl-4-oxo-3,4-di-
hydro-5H-imidazo[4,5-c]pyridin-5-yl)pentanamide;

Compound 12

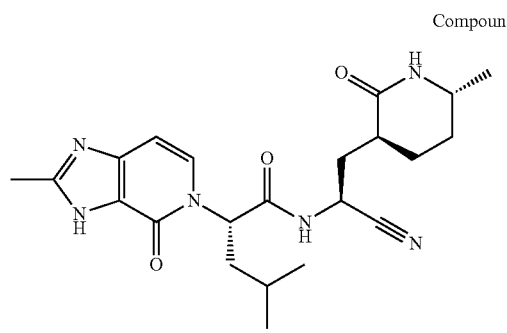

(2S)—N-{(1S)-1-cyano-2-[(3S,6R)-6-methyl-2-oxopiperi-
din-3-yl]ethyl}-4-methyl-2-(2-methyl-4-oxo-3,4-di-
hydro-5H-imidazo[4,5-c]pyridin-5-yl)pentanamide;

Compound 15

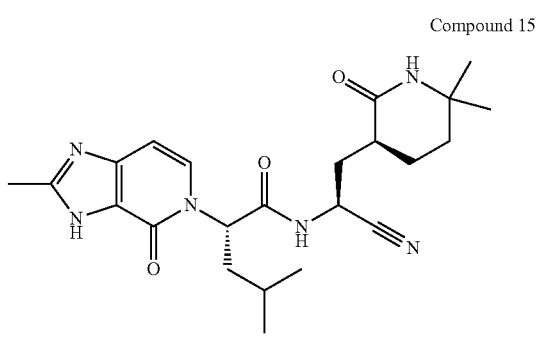

(2S)—N-{(1S)-1-cyano-2-[(3S)-6,6-dimethyl-2-oxopiperi-
din-3-yl]ethyl}-4-methyl-2-(2-methyl-4-oxo-3,4-di-
hydro-5H-imidazo[4,5-c]pyridin-5-yl)pentanamide;

Compound 13

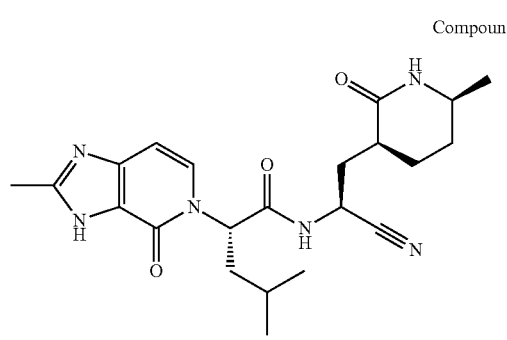

(2S)—N-{(1S)-1-cyano-2-[(3S,6S)-6-methyl-2-oxopiperi-
din-3-yl]ethyl}-4-methyl-2-(2-methyl-4-oxo-3,4-di-
hydro-5H-imidazo[4,5-c]pyridin-5-yl)pentanamide;

Compound 16

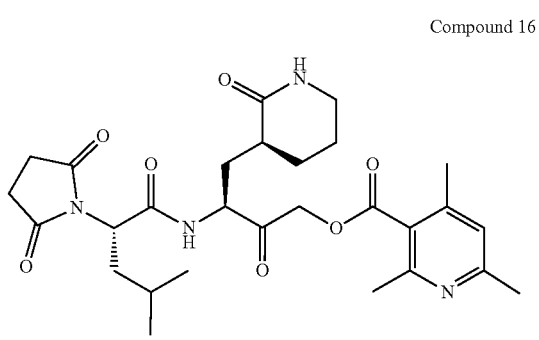 [SMILES: Cc1cc(C)c(C(=O)OCC(=O)[C@H](C[C@@H]2CCCNC2=O)NC(=O)[C@H](CC(C)C)N2C(=O)CCC2=O)c(C)n1]

(3S)-3-{[(2S)-2-(2,5-dioxopyrrolidin-1-yl)-4-methylpen-
tanoyl]amino}-2-oxo-4-[(3S)-2-oxopiperidin-3-yl]butyl
2,4,6-trimethylpyridine-3-carboxylate;

Compound 17

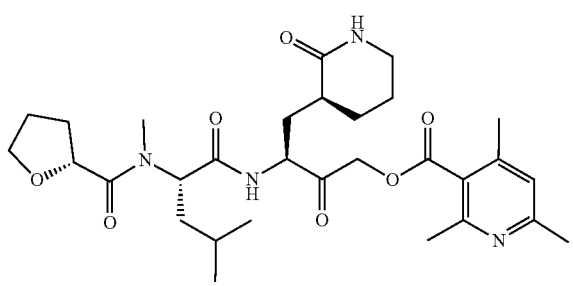

(3S)-3-({N-methyl-N-[(2R)-oxolane-2-carbonyl]-L-leucyl}amino)-2-oxo-4-[(3S)-2-oxopiperidin-3-yl]butyl 2,4,6-trimethylpyridine-3-carboxylate;

Compound 18

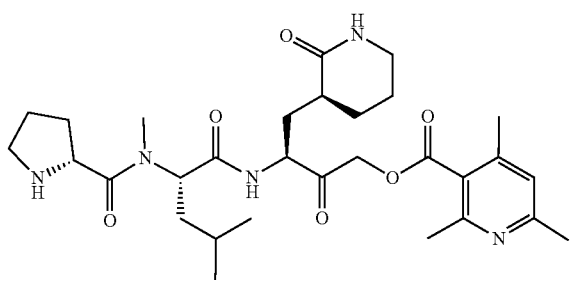

D-prolyl-$N^2$-methyl-N-{(2S)-3-oxo-1-[(3S)-2-oxopiperidin-3-yl]-4-[(2,4,6-trimethylpyridine-3-carbonyl)oxy]butan-2-yl}-L-leucinamide; and Compound 19

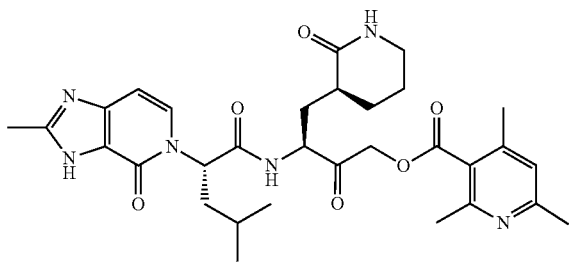

(3S)-3-{[(2S)-4-methyl-2-(2-methyl-4-oxo-3,4-dihydro-5H-imidazo[4,5-c]pyridin-5-yl)pentanoyl]amino}-2-oxo-4-[(3S)-2-oxopiperidin-3-yl]butyl 2,4,6-trimethylpyridine-3-carboxylate.

In certain embodiments, compounds of Formula (II) the present disclosure (e.g., compounds that find use in the methods of the present disclosure) include compounds selected from:

Compound 20

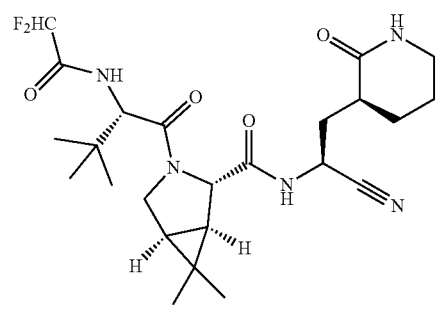

(1R,2S,5S)—N-{(1S)-1-cyano-2-[(3S)-2-oxopiperidin-3-yl]ethyl}-3-[N-(difluoroacetyl)-3-methyl-L-valyl]-6,6-dimethyl-3-azabicyclo[3.1.0]hexane-2-carboxamide;

Compound 21

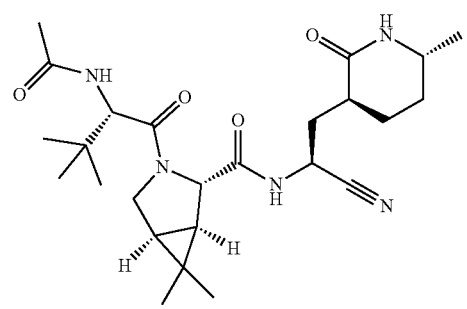

(1R,2S,5S)-3-(N-acetyl-3-methyl-L-valyl)-N-{(1S)-1-cyano-2-[(3S,6R)-6-methyl-2-oxopiperidin-3-yl]ethyl}-6,6-dimethyl-3-azabicyclo[3.1.0]hexane-2-carboxamide;

Compound 22

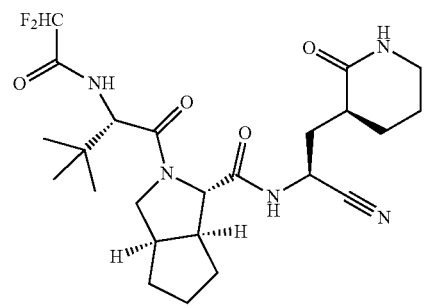

(1S,3aR,6aS)—N-{(1S)-1-cyano-2-[(3S)-2-oxopiperidin-3-yl]ethyl}-2-[(2S)-2-(2,2-difluoroacetamido)-3,3-dimethylbutanoyl]octahydrocyclopenta[c]pyrrole-1-carboxamide;

Compound 23

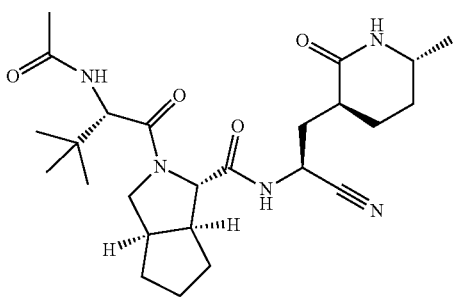

(1S,3aR,6aS)-2-[(2S)-2-acetamido-3,3-dimethylbutanoyl]-N-{(1S)-1-cyano-2-[(3S,6R)-6-methyl-2-oxopiperidin-3-yl]ethyl}octahydrocyclopenta[c]pyrrole-1-carboxamide; and Compound 24

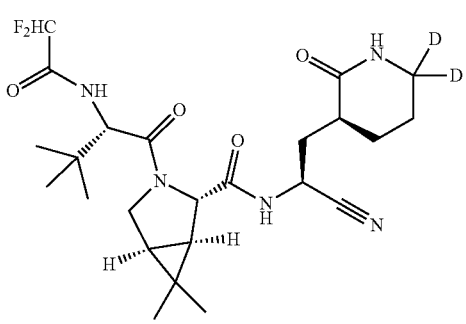

(1R,2S,5S)—N-{(1S)-1-cyano-2-[(3S)-2-oxo(6,6-$^2$H$_2$)piperidin-3-yl]ethyl}-3-[N-(difluoroacetyl)-3-methyl-L-valyl]-6,6-dimethyl-3-azabicyclo[3.1.0]hexane-2-carboxamide.

The compounds described herein can be isolated by procedures known to those skilled in the art. The compounds described herein may be obtained, for instance, by a resolution technique or by chromatography techniques (e.g., silica gel chromatography, chiral chromatography, etc.). As used herein, the term "isolated" refers to compounds that are non-naturally occurring and can be obtained or purified from synthetic reaction mixtures. Isolated compounds may find use in the pharmaceutical compositions and methods of treatment described herein.

The compounds described also include isotopically labeled compounds where one or more atoms have an atomic mass different from the atomic mass conventionally found in nature. Examples of isotopes that may be incorporated into the compounds disclosed herein include, but are not limited to, $^2$H (deuterium, D), $^3$H (tritium, T), $^{11}$C, $^{13}$C, $^{14}$C, $^{15}$N, $^{18}$O, $^{17}$O, etc. Thus, the disclosed compounds may be enriched in one or more of these isotopes relative to the natural abundance of such isotope. By way of example, deuterium ($^2$H; D) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%. In some embodiments, one or more (e.g., 1, 2, 3, 4, 5, 6, 7 or more) hydrogen atoms of a substituent group (e.g., an R-group) of any one of the subject compounds described herein are substituted with a deuterium.

Methods of Use

The compounds of the present disclosure find use in treatment of a condition or disease in a subject that is amenable to treatment by administration of the compound. Thus, in some embodiments, provided are methods that include administering to a subject a therapeutically effective amount of any of the compounds of the present disclosure. In certain aspects, provided are methods of delivering a compound to a target site in a subject, the method including administering to the subject a pharmaceutical composition including any of the compounds of the present disclosure, where the administering is effective to provide a therapeutically effective amount of the compound at the target site in the subject.

The subject to be treated can be one that is in need of therapy, where the subject to be treated is one amenable to treatment using the compounds disclosed herein. Accordingly, a variety of subjects may be amenable to treatment using the compounds disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). In some instances, the mammal is selected from a companion animal and livestock. In some instances, the mammal is feline. In some instances, the mammal is a human.

The present disclosure provides methods that include delivering a compound of the present disclosure to an individual having a disease, such as methods that include administering to the subject a therapeutically effective amount of a compound of the present disclosure. The methods are useful for treating a wide variety of conditions and/or symptoms associated with a disease. In the context of disease, the term "treating" includes one or more (e.g., each) of: reducing the severity of one or more symptoms, inhibiting the progression, reducing the duration of one or more symptoms, and ameliorating one or more symptoms associated with the disease.

In certain embodiments, methods of the present disclosure include inhibiting a Baltimore Group IV RNA virus in a cell infected with a Baltimore Group IV RNA virus, wherein the method includes contacting the cell with a compound of the present disclosure. In some instances, the contacting includes delivering the compound into the cytosol of the cell by any suitable means. In some instances, the compounds of the present disclosure are effective for inhibiting the viral activity of a Baltimore Group IV RNA virus including any of, e.g., the attachment, penetration, uncoating, replication, assembly, and release of the virus. In some instances, a compound of the present disclosure is effective for treating a Baltimore Group IV RNA virus infection by inhibiting the activity of a protease. The protease may be required for the activity of the virus, e.g., the attachment, penetration, uncoating, replication, assembly, and/or release of the virus. In some instances, compounds of the present disclosure are effective for inhibiting the activity of the protease by inhibiting, e.g., blocking or chemically reacting with, a catalytic domain or catalytic residue(s) of the protease. In some instances, compounds of the present disclosure inhibit the activity of the protease by forming a covalent bond with a catalytic domain or catalytic residue(s). The catalytic domain or catalytic residue(s) may be present in the active site of the protease. In some instances, the protease is a cysteine protease. In some instances, the protease is 3-chymotrypsin protease (3CP). In some instances, the protease is 3-chymotrypsin-like protease (3CLP).

In certain embodiments, methods of the present disclosure include administering a compound of the present disclosure to a subject, where the administering is effective for treating a disease caused by a Baltimore Group IV RNA virus. The methods may include a method of treating a Baltimore Group IV RNA virus infection in a mammal, the method comprising administering to the mammal an effective amount of a compound of the present disclosure. In some embodiments, the methods involve administering an effective amount of a compound according to the present disclosure, a pro-drug thereof or a pharmaceutically acceptable salt thereof to a subject. In certain embodiments, the methods include identifying a subject with a Baltimore Group IV RNA virus infection, e.g., a coronavirus infection, a rhinovirus infection, a norovirus infection, and administering a compound of the present disclosure, a pro-drug thereof or a pharmaceutically acceptable salt thereof to the subject. In some instances, the methods include a step (a) of testing a patient for a Baltimore Group IV RNA virus, e.g., before any treatment is administered. The methods may then include step (b) of administering a compound of the present disclosure, a pro-drug thereof or a pharmaceutically acceptable salt thereof to the subject according to any of the embodiments described herein.

A compound of the present disclosure may be administered at any point during a subject's infection with a Baltimore Group IV RNA virus. In certain embodiments, the subject has, has had, is suspected to have, or is suspected to have had a Baltimore Group IV RNA virus infection. A subject with a Baltimore Group IV RNA virus infection may exhibit one or more symptoms including, e.g., a cough, fever or chills, shortness of breath, fatigue, muscle or body aches, new loss of taste or smell, sore throat, headache, congestion, nasal discharge, nausea, vomiting, diarrhea, stomach pain, chest pain or pressure, confusion, inability to wake or stay awake, and bluish lips or face. In some cases, the subject is asymptomatic. In some cases, a subject with a Baltimore Group IV RNA virus infection exhibits one or more syndromes or acute conditions including, e.g., organ failure, acute respiratory distress syndrome, acute kidney injury, and thrombosis. In certain embodiments, the subject has or is expected to develop symptoms associated with a cytokine response, e.g., a cytokine storm caused by the overproduction of inflammatory cytokines. In some cases, the patient may have signs of respiratory distress, e.g., a cough, but does not have acute respiratory distress syndrome. In these embodiments, the patient may not be in intensive care. The patient may have or may have had one or more other lung diseases in the past. For example, in some cases, the patient has or has a history of having asthma, pneumothorax, atelectasis, bronchitis, chronic obstructive pulmonary disease, lung cancer or pneumonia. In some cases, the infection is a SARS infection. In some cases, the infection is a MERS infection. In some cases, the infection is a COVID-19 infection. In some instances, the subject receives multiple administrations of a compound over a period including, e.g., days, weeks, or months.

The administering can be done any convenient way. Generally, administration is, for example, oral, buccal, parenteral (e.g., intravenous, intraarterial, subcutaneous), intraperitoneal (i.e., into the body cavity), topically, e.g., by inhalation or aeration (i.e., through the mouth or nose), or rectally systemic (i.e., affecting the entire body). For example, the administration may be systemic, e.g., orally (via injection of tablet, pill or liquid) or intravenously (by injection or via a drip, for example). In other embodiments, the administering can be done by pulmonary administration, e.g., using an inhaler or nebulizer. Compounds of the present disclosure or composition comprising the compounds may be administered in dosage unit formulations containing conventional non-toxic pharmaceutically acceptable carriers, adjuvants, and vehicles as desired. The term "topically" may include injection, insertion, implantation, topical application, or parenteral application.

The virus inhibited by the methods may be any of the Baltimore Group IV RNA viruses. In some instances, the Baltimore Group IV RNA virus is selected from picornavirus, norovirus, and coronavirus. In some instances, the Baltimore Group IV RNA virus is selected from enterovirus, rhinovirus, coxsackie virus, norovirus and coronavirus. In some instances, the Baltimore Group IV RNA virus is selected from norovirus, and coronavirus. In some instances, the Baltimore Group IV RNA virus is human norovirus. In some embodiments, the Baltimore Group IV RNA virus is coronavirus. In certain embodiments, the coronavirus is one that causes disease in mammals. In certain embodiments, the coronavirus causes disease in companion animals or livestock. In certain embodiments, the coronavirus is a feline coronavirus. In certain embodiments, the coronavirus is feline infectious peritonitis. In certain embodiments, the coronavirus is a human coronavirus. In certain embodiments, the coronavirus is selected from Severe Acute Respiratory Syndrome coronavirus 2 (SARS-CoV-2), Severe Acute Respiratory syndrome coronavirus 1 (SARS-CoV-1) and Middle Eastern Respiratory syndrome-related coronavirus (MERS-CoV).

Pharmaceutical Compositions

In certain embodiments, the disclosed compounds are useful for the treatment of a disease or disorder. Accordingly, pharmaceutical compositions comprising at least one disclosed compound are also described herein. For example, the present disclosure provides pharmaceutical compositions that include a therapeutically effective amount of a compound of the present disclosure (or a pharmaceutically acceptable salt or solvate or hydrate or stereoisomer thereof) and a pharmaceutically acceptable excipient.

A pharmaceutical composition that includes a subject compound may be administered to a patient alone, or in combination with other supplementary active agents. For example, one or more compounds according to the present disclosure can be administered to a patient with or without supplementary active agents. The pharmaceutical compositions may be manufactured using any of a variety of processes, including, but not limited to, conventional mixing, dissolving, granulating, dragee-making, levigating, emulsifying, encapsulating, entrapping, lyophilizing, and the like. The pharmaceutical composition can take any of a variety of forms including, but not limited to, a sterile solution, suspension, emulsion, spray dried dispersion, lyophilisate, tablet, microtablets, pill, pellet, capsule, powder, syrup, elixir or any other dosage form suitable for administration.

A compound of the present disclosure may be administered to a subject using any convenient means capable of resulting in the desired reduction in disease condition or symptom. Thus, a compound can be incorporated into a variety of formulations for therapeutic administration. More particularly, a compound can be formulated into pharmaceutical compositions by combination with appropriate pharmaceutically acceptable excipients, carriers or diluents, and may be formulated into preparations in solid, semi-solid, liquid or gaseous forms, such as tablets, capsules, powders, granules, ointments, solutions, suppositories, injections, inhalants, aerosols, and the like.

Formulations for pharmaceutical compositions are described in, for example, Remington's Pharmaceutical Sciences, by E. W. Martin, Mack Publishing Co., Easton, Pa., 19th Edition, 1995, which describes examples of formulations (and components thereof) suitable for pharmaceutical delivery of the disclosed compounds. Pharmaceutical compositions that include at least one of the compounds can be formulated for use in human or veterinary medicine. Particular formulations of a disclosed pharmaceutical composition may depend, for example, on the mode of administration and/or on the location of the subject to be treated. In some embodiments, formulations include a pharmaceutically acceptable excipient in addition to at least one active ingredient, such as a compound of the present disclosure. In other embodiments, other medicinal or pharmaceutical agents, for example, with similar, related or complementary effects on the disease or condition being treated can also be included as active ingredients in a pharmaceutical composition.

Pharmaceutically acceptable carriers useful for the disclosed methods and compositions may depend on the particular mode of administration being employed. In addition to biologically neutral carriers, pharmaceutical compositions to be administered can optionally contain non-toxic auxiliary substances (e.g., excipients), such as wetting or emulsifying agents, preservatives, and pH buffering agents, and the like. The disclosed pharmaceutical compositions may be formulated as a pharmaceutically acceptable salt of a disclosed compound.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, excipient, carrier or vehicle. The specifications for a compound depend on the particular compound employed and the effect to be achieved, and the pharmacodynamics associated with each compound in the subject.

The dosage form of a disclosed pharmaceutical composition may be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions that include a subject compound may be formulated in unit dosage form suitable for individual administration of precise dosages. The amount of active ingredient administered may depend on the subject being treated, the severity of the affliction, and the manner of administration, and is known to those skilled in the art. In certain instances, the formulation to be administered contains a quantity of the compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual compound may be administered at the same time as another therapeutic compound or sequentially, in any order thereof.

A disclosed compound can be administered alone, as the sole active pharmaceutical agent, or in combination with one or more additional compounds of the present disclosure or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of the present disclosure optionally include other therapeutic agents. Accordingly, certain embodiments are directed to such pharmaceutical compositions, where the composition further includes a therapeutically effective amount of an agent selected as is known to those of skill in the art.

Methods of Administration

The subject compounds find use for treating a disease or disorder in a subject. The route of administration may be selected according to a variety of factors including, but not limited to, the condition to be treated, the formulation and/or device used, the subject to be treated, and the like. Routes of administration useful in the disclosed methods include, but are not limited to, oral and parenteral routes, such as intravenous (iv), intraperitoneal (ip), rectal, topical, ophthalmic, nasal, intrathecal, and transdermal. Formulations for these dosage forms are described herein.

An effective amount of a subject compound may depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (e.g., patient) being treated. For example, this may be the amount of a subject compound necessary to prevent, inhibit, reduce or relieve a disease or disorder in a subject. Ideally, a therapeutically effective amount of a compound is an amount sufficient to prevent, inhibit, reduce or relieve a disease or disorder in a subject without causing a substantial cytotoxic effect on host cells in the subject.

Therapeutically effective doses of a subject compound or pharmaceutical composition can be determined by one of skill in the art. For example, in some instances, a therapeutically effective dose of a compound or pharmaceutical composition is administered with a goal of achieving local (e.g., tissue) concentrations that are at least as high as the $EC_{50}$ of an applicable compound disclosed herein.

The specific dose level and frequency of dosage for any particular subject may be varied and may depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

In some embodiments, multiple doses of a compound are administered. The frequency of administration of a compound can vary depending on any of a variety of factors, e.g., severity of the symptoms, condition of the subject, etc. For example, in some embodiments, a compound is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds, including compounds that are not commercially available, can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

In certain embodiments, compounds of the present disclosure (e.g., compounds of formula (I), (Ia) and (II)) are synthesized using conventional methods and conditions, as depicted in the combination of Scheme 1 and Scheme 2 or Scheme 3. Scheme 1 shows the formation of a component of a compound of the present disclosure, while Scheme 2 depicts the assembly of the complete compound for formula (I) and (Ia) and Scheme 3 depicts the assembly of the complete compound for formula (II). Components of compounds of the present disclosure are synthesized using conventional methods and conditions, as depicted in Scheme 1:

Scheme 1

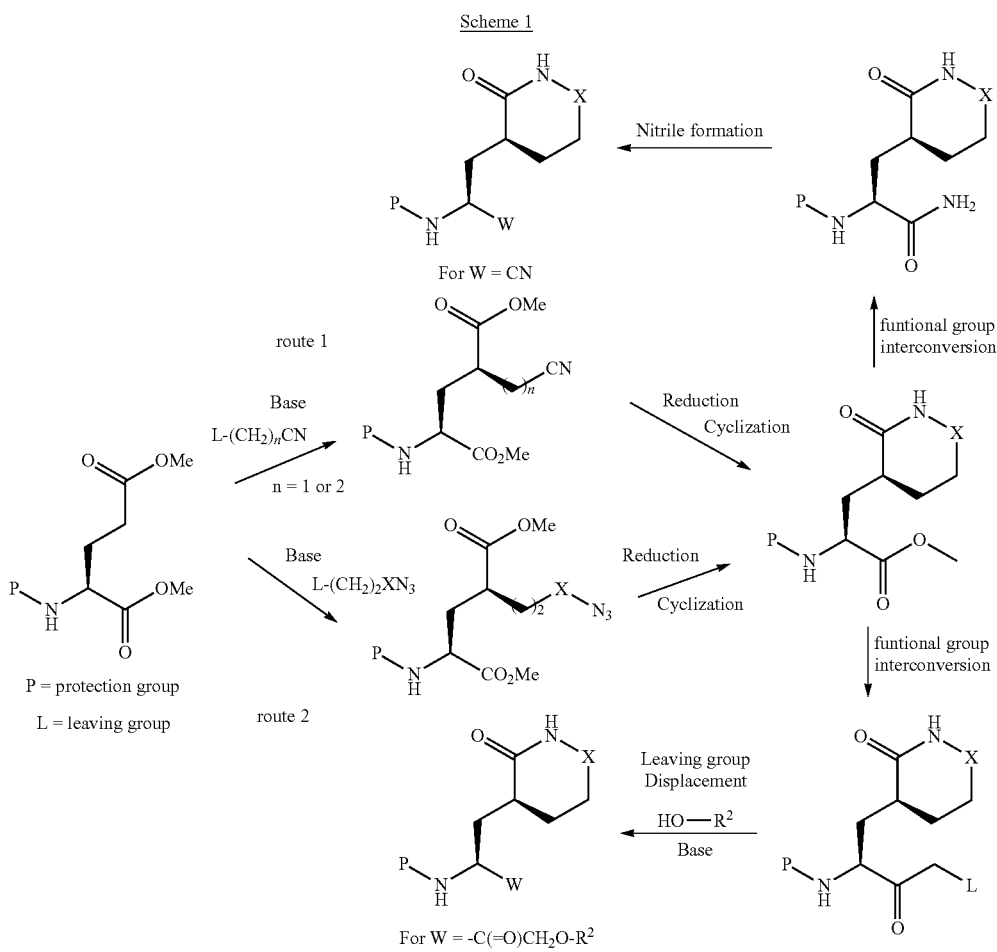

wherein $R^2$, W and X are as defined herein.

The starting materials and reagents employed in Scheme 1 may be obtained commercially or through conventional techniques. The scheme is an example of a method to generate components of compounds of the present disclosure where the exact steps and materials will depend on the functional groups present. The selection of the starting materials, reagent, substrates, base, protecting group, solvent and leaving group can be accomplished by one of ordinary skilled in the art. A nitrogen protected, a non-limiting example is a t-butylcarbonate (Boc) group, diester of glutamic acid, a non-limiting example is the dimethyl ester, is reacted with base, such as lithium hexamethyldisilylamide, and then a nitrile containing electrophile, non-limiting examples are bromoacetonitrile and 3-bromopropionitrile (route 1). Reduction of the resulting nitrile, such as in the presence of cobalt (II) chloride and sodium borohydride, followed by cyclization to the corresponding lactam. Alternatively, a nitrogen protected, a non-limiting example is a t-butylcarbonate (Boc) group, diester of glutamic acid, a non-limiting example is the dimethyl ester, is reacted with base, such as lithium hexamethyldisilylamide, and then a azide containing electrophile (route 2). Reduction of the resulting azide, such as by hydrogenolysis with a palladium catalyst in the presence of hydrogen or stannous chloride, followed by cyclization will form the corresponding lactam. Other masked nitrogens and electrophiles, such as different leaving groups, similar to that depicted by route 1 or 2 can be utilized by one skilled in the art to produce the corresponding lactam with the appropriate X. The ester of the corresponding lactam can be converted to the primary amide, for example saponification with hydroxide, such as lithium hydroxide, and the resulting carboxylic acid coupled with ammonia using base and a coupling agent, such as with 1-[bis(dimethylamino)methylene]-1H-1,2,3-triazolo[4,5-b]pyridinium 3-oxide hexafluorophosphate (HATU). Conversion of the amide to a nitrile, for W=CN, is accomplished using a dehydrating agent, such as $POCl_3$ or trifluoroacetic anhydride. Alternatively, for W=—C(=O)$CH_2$O—$R^2$ the ester intermediate can be interconverted to a substituted methyl ketone. There are numerous methods described in the literature that one skilled in the art could follow. One, non-limiting example, is to generate the methyl ketone with a leaving group (L), such as a chloro by contacting the ester with t-butylmagnesium chloride and sodium chloroacetate in the presence of base. The resulting leaving group substituted methyl ketone, such as with a chloro, is reacted with the salt of the $R^2$OH group, which is generated by reacting $R^2$OH with a suitable base, such as sodium hydride or potassium tert-butoxide. The resulting displacement of the leaving group generates the intermediate where W=—C(=O)$CH_2$O—$R^2$.

Compounds of the present disclosure of formula (I) and (Ia) are synthesized using the intermediate generated in Scheme 1 with conventional methods and conditions, as depicted in Scheme 2:

Scheme 2

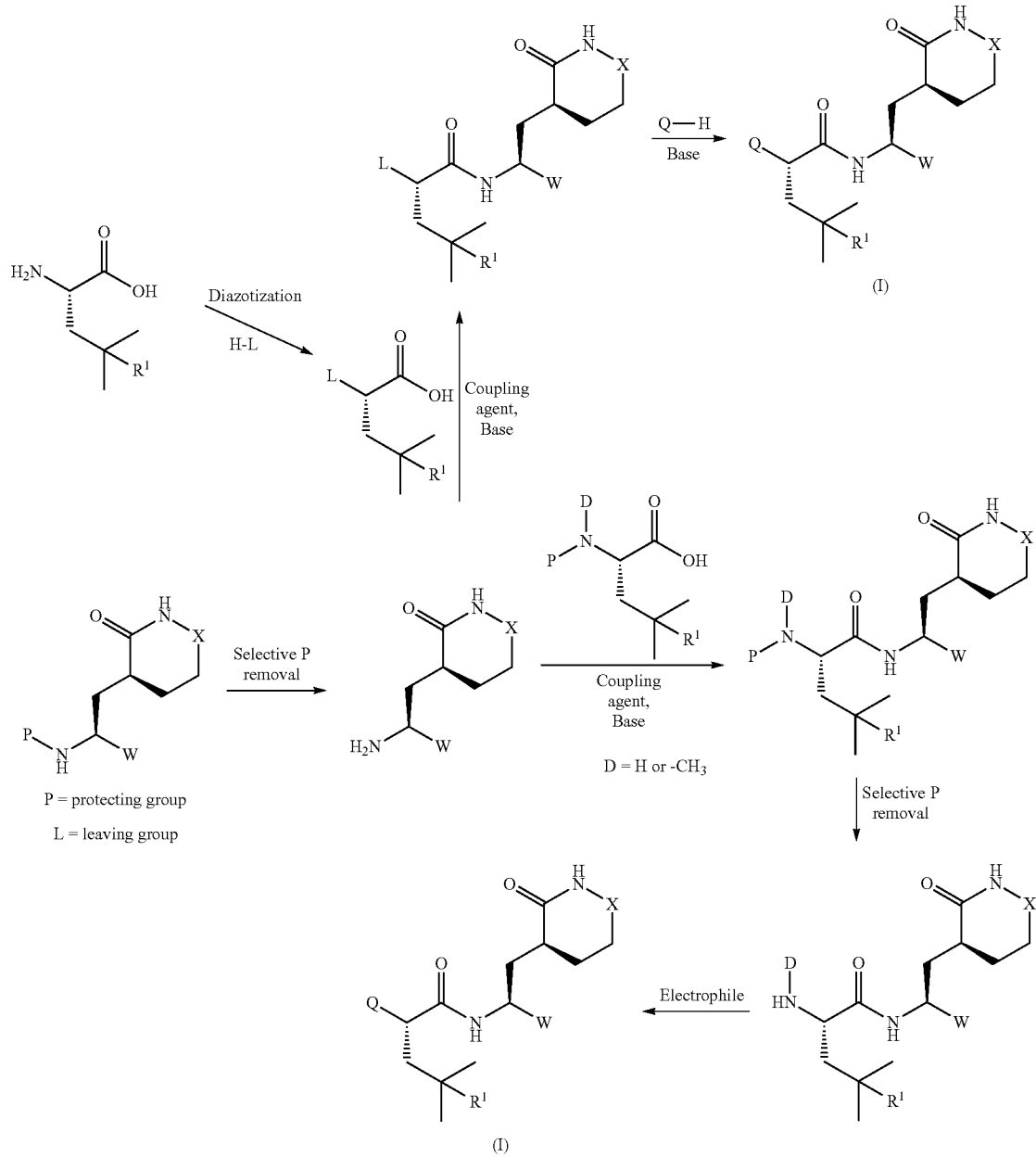

wherein R¹, Q, W, X are as defined herein.

The starting materials and reagents employed in Scheme 2 may be obtained commercially or through techniques known to one of ordinary skill in the art. The scheme is an example of a method to generate compounds of the present disclosure where the exact steps and materials will depend on the functional groups present. The selection of the starting materials, reagent, substrates, base, protecting group, solvent and leaving group can be accomplished by one of ordinary skilled in the art. Removal of the nitrogen protecting group (P) is well documented in the literature and is of common knowledge to those skilled in the art. For example, removal of a Boc group can be accomplished with acid, such as trifluoroacetic acid or hydrochloric acid. Coupling the resulting nitrogen, amine or ammonium, to a protected amino acid can be accomplished with a coupling agent, such as HATU, and an appropriate base, for example triethylamine or N-methylmorpholine. Different routes to formula (I) can be utilized depending on coupling partner as understood by one of ordinary skill in the art and two are shown as non-limiting examples in Scheme 2. For the first (top route) the coupling partner also has a leaving group, such as bromide that can be generated from the corresponding amino acid by diazotization with a reagent such as sodium nitrite in the presence of a strong acid such as hydrobromic acid. That product which acts as an electrophile is reacted with Q-H which is pretreated with an appropriate base, such as 1,8-diazobicyclo[5.4.0]undec-7-ene or lithium diisopropylamide, to produce formula (I). Alternatively, the second route example shown in Scheme 2 the coupling proceeds with a suitably protected amino acid, such as with a Boc group, to form the dipeptide. Removal of the nitrogen protecting group (P) is well documented in the literature and is of common knowledge to those of ordinary skill in the art. For example, removal of a Boc group can be accomplished with acid, such as trifluoroacetic acid or hydrochloric acid. The resulting amine generated after neutralization or treatment with a suitable base is then reacted with the corresponding electrophile and either directly this produces the Q described herein or in some cases one or two additional steps, for example deprotection or cyclization, are required that are known to those or ordinary skill in the art in order to generate the compound of formula (I).

Compounds of the present disclosure of formula (II) are synthesized using the intermediate generated in Scheme 1 with conventional methods and conditions, as depicted in Scheme 3:

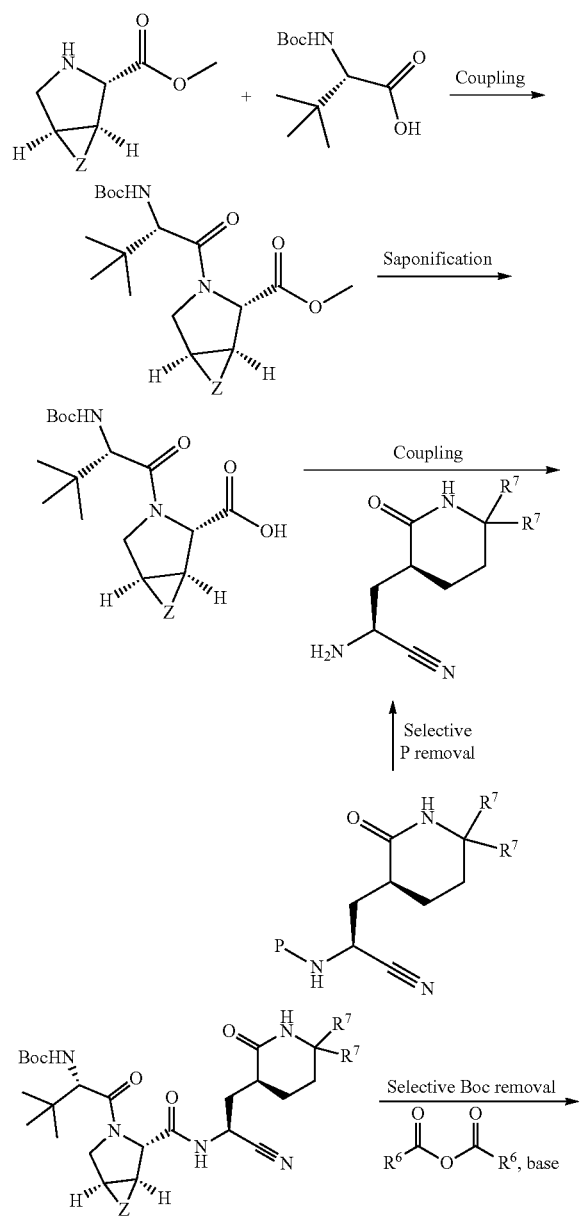

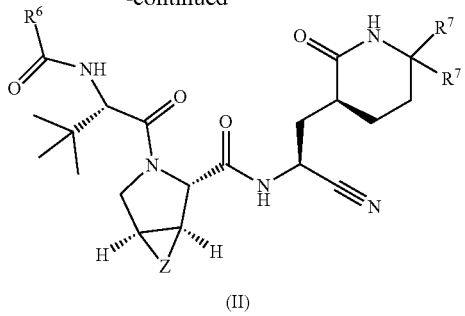

wherein $R^6$, $R^7$ and Z are as defined herein.

The starting materials and reagents employed in Scheme 3 may be obtained commercially or through techniques known to one of ordinary skill in the art. The scheme is an example of a method to generate compounds of the present disclosure where the exact steps and materials will depend on the functional groups present. The bicyclicproline and Boc-protected t-butylglycine are coupled using, as a non-limiting example, HATU and a suitable base such as triethylamine or N-methylmorpholine. The conversion of the ester to the carboxylic acid can be accomplished by saponification, such as with lithium hydroxide, followed by careful acidification to approximately pH 4, such as with a sodium bisulfate solution. Coupling of this acid to the deprotected intermediate from Scheme 1 (where X=—C($R^7$)$_2$—) using a suitable coupling agent, for example HATU, in the presence of a base, for example trimethylamine or N-methylmorpholine, will produce the Boc-protected tripeptide mimic. The removal of the Boc group, such by treatment with trifluoroacetic acid or hydrochloride, followed by the reaction of the liberated nitrogen in the presence of base, such as triethylamine or N-methylmorpholine, with the anhydride of $R^6$ or $R^6CO_2H$ with a coupling agent, such as HATU, will generate formula (II).

Schemes 1, 2 and 3 are meant to be by way of non-limiting examples only, and one of ordinary skill in the art will understand that alternate reagents, solvents, order of reactions or starting materials can be used to make compounds of the present disclosure and/or other intermediates or compounds contained herein.

Example 1: Synthesis of Compounds

All reagents and solvents were used as purchased from commercial sources. Moisture sensitive reactions were carried out under a nitrogen atmosphere. Reactions were monitored by TLC using pre-coated silica gel aluminum plates containing a fluorescent indicator (F-254). Detection was done with UV (254 nm). Alternatively, the progress of a reaction was monitored by LC/MS. Specifically, but without limitation, the following abbreviations were used, in addition to the other ones described herein, in the examples: Boc (tert-butoxycarbonyl); Boc$_2$O (di-tert-butyl dicarbonate); cat. (catalytic amount); DCM (dichloromethane); dioxane (1,4-dioxane); DMF (N,N-dimethylformamide); CDI (1,1'-carbonyldiimidazole); EDCI (N-ethyl-N'-carbodiimide); EtOH (ethanol); ether or Et$_2$O (diethyl ether); Et$_3$N (triethylamine); EtOAc (ethyl acetate); HATU (1-[bis(dimethylamino)methylene]-1H-1,2,3-triazolo[4,5-b]pyridinium 3-oxide hexafluorophosphate or N-[(dimethylamino)-1H-1,2,3-triazolo-[4,5-b]pyridin-1-ylmethylene]-N-methylmethanaminium hexafluorophosphate N-oxide); hex (hexanes);

MeCN (acetonitrile); MeOH (methanol); μW (microwave); N-methylmorpholine (NMM); NaOtBu (sodium tert-butoxide); O/N (overnight); RT or rt (room or ambient temperature); TBS (tert-butyldimethylsilyl); t-BuMgCl (tert-butylmagnesium chloride); TFA (trifluoroacetic acid); TFAA (trifluoroacetic anhydride); THF (tetrahydrofuran). $^1$H NMR spectra were recorded at RT with a Bruker Avance III 600 MHz NMR spectrometer equipped with a Bruker's 5 mm PABBO probe. Chemical shifts are reported in ppm downfield from tetramethylsilane using residual solvent signals as internal reference. NMR data were processed utilizing ACD/Spectrus processor (v2016.1.1, ACD/Labs Inc.). Nomenclature for the naming of compounds, such as for Compound Examples and intermediate compounds, were performed using ACD/Name (Chemists' Version from ACD/Labs Inc.) or Bruker TopSpin 4.0.6 to generate the IUPAC-style names. Naming of commercial or literature compounds utilized SciFinder, ACD/Names, and common or trivial names known to those skilled in the art.

The LC/MS system used for monitoring the progress of reactions, assessing the purity (absorbance at 254 nm) and identity of the product consisted of Dionex ULTIMATE 3000 uHPLC module and Thermo Scientific LTQ XL mass-spectrometer with electrospray ionization and Ion-Trap type of detector (alternating positive-negative mode). Separation was performed with Thermo Scientific™ Accucore™ aQ C18 Polar Endcapped LC column (100 mm×2.1 mm; particle size 2.6 m, 80 Å). The column was maintained at 35° C. Commercial HPLC-grade methanol and domestic 'millipore (Milli-Q)' water used for chromatography were modified by adding 0.1% (v/v) of formic acid. The eluent was delivered with constant flow rate of 0.4 mL/min, column was equilibrated for 5 min with the corresponding eluent prior to injection of the sample (1 μL) and one of the following separation conditions were used:

Eluent Systems:
  A—Gradient of Methanol-Water, 45 to 95% in 5.25 min, followed by 5 min of isocratic MeOH-water 95%;
  B—Gradient of Methanol-Water, 30 to 65% in 4.75 min, then to 95% in 2.5 min, followed by 4 min of isocratic MeOH-water 95%; and
  C—Gradient of MeOH-Water, 15% to 65% in 5 min, 65% to 95% in 2.5 min, followed by 4 min of isocratic MeOH-water 95%.

Compound 1

Synthesis of (2S)—N-{(1S)-1-cyano-2-[(3S)-2-oxopiperidin-3-yl]ethyl}-2-(1,3-dioxo-1,3-dihydro-2H-isoindol-2-yl)-4-methylpentanamide, 1

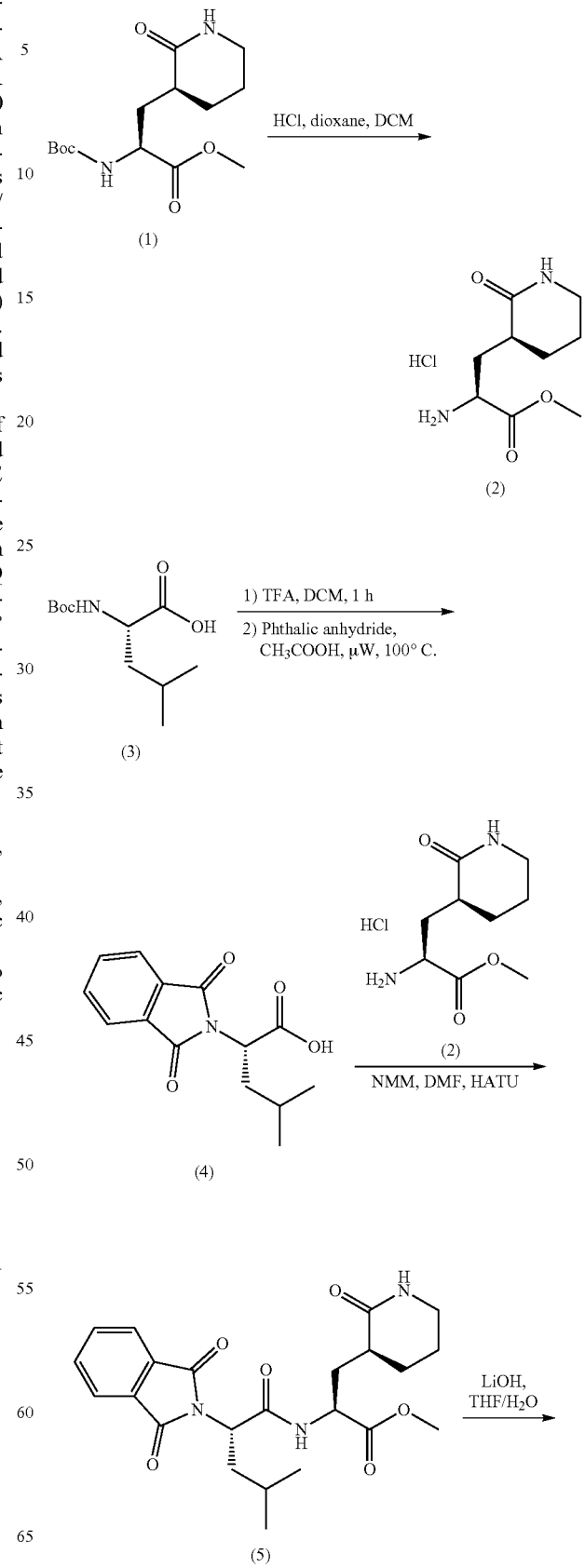

Scheme 4

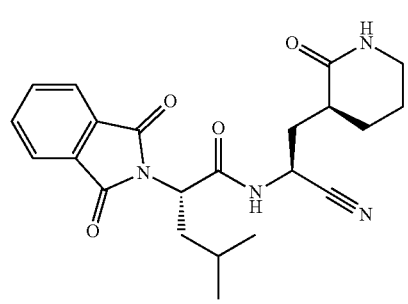

Compound 1 was synthesized as in Scheme 4.

-continued

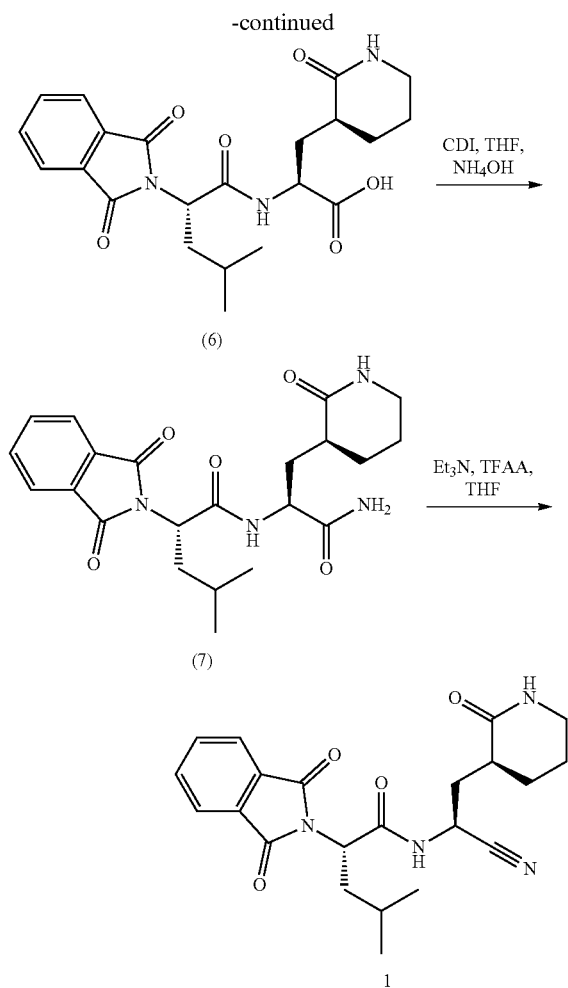

Preparation of methyl 3-[(3S)-2-oxopiperidin-3-yl]-L-alaninate hydrochloride salt, (2). To a solution of methyl N-(tert-butoxycarbonyl)-3-[(3S)-2-oxopiperidin-3-yl]-L-alaninate (1) (505.3 mg, 1.682 mmol) [prepared according to Y. Zhai et al Journal of Medicinal Chemistry, year 2015, volume 58, pages 9414-9420] in DCM (20 mL) was cooled using an ice-water bath and then 4 M HCl in 1,4-dioxane (5 mL) was added. After 30 min, the ice bath was removed and the mixture warmed to room temperature. After overnight, the mixture was concentrated under reduced pressure. Co-evaporated with DCM (3×25 mL), and drying under reduced pressure for 1 h afforded the hydrochloride salt (2) as an off-white solid (398.1 mg). This material was used without further purification in the next step.

Preparation of (2S)-2-(1,3-dioxo-1,3-dihydro-2H-isoindol-2-yl)-4-methylpentanoic acid, (4). A solution of N-(tert-butoxycarbonyl)-L-leucine (3) (231 mg, 0.999 mmol) in DCM (10 mL) was added TFA (3 mL) slowly. After 1 h, the mixture was concentrated under reduced pressure. The resulting residue was mixed with phthalic anhydride (163 mg, 1.10 mmol), acetic acid (5 mL) and the mixture was irradiated in a microwave reactor for 1 h at 100° C. After concentrating, the product was purified by column chromatography on silica gel with a gradient of 50 to 100% EtOAc in hexanes, which generated (4) (118 mg, 45% yield) as a gum. LC/MS: Eluent system A (retention time: 4.88 min); ESI-MS: 262 [M+H]$^+$, 260 [M−H]$^−$.

Preparation of methyl N-[(2S)-2-(1,3-dioxo-1,3-dihydro-2H-isoindol-2-yl)-4-methylpentanoyl]-3-[(3S)-2-oxopiperidin-3-yl]-L-alaninate, (5). To a solution of (2S)-2-(1,3-dioxo-1,3-dihydro-2H-isoindol-2-yl)-4-methylpentanoic acid (4) (118 mg, 0.452 mmol) and methyl 3-[(3S)-2-oxopiperidin-3-yl]-L-alaninate-hydrogen chloride (2) (107 mg, 0.452 mmol) in anhydrous DMF (5 mL) cooled in an ice bath was added HATU (269 mg, 0.708 mmol). Then NMM (0.35 mL, 3.8 mmol) was added. After 45 min, water (5 mL) was added and the resulting mixture was extracted with EtOAc (3×50 mL). The combined organic layer was washed with brine (10 mL), dried over anhydrous $Na_2SO_4$, filtered, and concentrated under reduced pressure. The product was purified by column chromatography on silica gel with a gradient of 50 to 100% EtOAc in hexanes, which generated (5) (164 mg, 82% yield) as a gum. LC/MS: Eluent system A (retention time: 4.73 min); ESI-MS: 444 [M+H]$^+$.

Preparation of N-[(2S)-2-(1,3-dioxo-1,3-dihydro-2H-isoindol-2-yl)-4-methylpentanoyl]-3-[(3S)-2-oxopiperidin-3-yl]-L-alanine, (6). To a solution of methyl N-[(2S)-2-(1,3-dioxo-1,3-dihydro-2H-isoindol-2-yl)-4-methylpentanoyl]-3-[(3S)-2-oxopiperidin-3-yl]-L-alaninate (5) (164 mg, 0.370 mmol) in THF (5 mL) cooled in an ice bath was added LiOH (44.3 mg, 1.85 mmol, in 2 mL of $H_2O$). After 1 h, a 1.0 M aqueous HCl solution was added until the pH of the mixture was 3, and then the mixture was extracted with DCM (3×20 mL). The combined organic layer was dried over $Na_2SO_4$, filtered and concentrated under reduced pressure, which generated (6) (81.6 mg, 51% yield) as a gum. LC/MS: Eluent system B (retention time: 4.17 min); ESI-MS: 448 [M+H+$H_2O$]$^+$.

Preparation of (2S)—N-{(2S)-1-amino-1-oxo-3-[(3S)-2-oxopiperidin-3-yl]propan-2-yl}-2-(1,3-dioxo-1,3-dihydro-2H-isoindol-2-yl)-4-methylpentanamide, (7). To a solution of N-[(2S)-2-(1,3-dioxo-1,3-dihydro-2H-isoindol-2-yl)-4-methylpentanoyl]-3-[(3S)-2-oxopiperidin-3-yl]-L-alanine (5) (81 mg, 0.19 mmol) in THF (5 mL) was added carbonyldiimidazole (CDI) (62 mg, 0.38 mmol). After 15 min, an aqueous ammonium hydroxide solution (28-30%) (0.2 mL, 4.8 mmol) was added. After 1 h, water (5 mL) was added and the resulting mixture was extracted with EtOAc (3×50 mL). The combined organic phase was dried over $Na_2SO_4$, filtered and concentrated under reduced pressure. The product was purified by column chromatography on silica gel with a gradient of 0 to 10% MeOH in $CHCl_3$, which generated (7) (63 mg, 78% yield) as a white foam. LC/MS: Eluent system B (retention time: 6.52 min); ESI-MS: 429 [M+H]$^+$.

Preparation of (2S)—N-{(1S)-1-cyano-2-[(3S)-2-oxopiperidin-3-yl]ethyl}-2-(1,3-dioxo-1,3-dihydro-2H-isoindol-2-yl)-4-methylpentanamide, 1. To a solution of (2S)—N-{(2S)-1-amino-1-oxo-3-[(3S)-2-oxopiperidin-3-yl]propan-2-yl}-2-(1,3-dioxo-1,3-dihydro-2H-isoindol-2-yl)-4-methylpentanamide (7) (63.3 mg, 0.148 mmol) and $Et_3N$ (44.9 mg, 0.443 mmol) in THF (5 mL) cooled in an ice bath was added trifluoroacetic anhydride (TFAA) (62.2 mg, 0.296 mmol). After 15 min, water (5 mL) was added and the resulting mixture was extracted with DCM (3×50 mL). The combined organic layer was dried over $Na_2SO_4$, filtered and concentrated under reduced pressure. The product was purified by column chromatography on silica gel with a gradient of 0 to 10% MeOH in $CHCl_3$, which generated 1 (16.2 mg, 26% yield) as a white solid. $^1$H NMR (600 MHz, DMSO-$d_6$) δ 8.91 (d, J=7.9 Hz, 1H), 7.97-7.83 (m, 4H), 7.47 (br s, 1H), 5.05-5.00 (m, 1H), 4.74 (dd, J=4.1, 11.3 Hz, 1H), 3.31-3.20 (m, 2H), 3.13-3.04 (m, 2H), 2.20-2.15 (m, 1H), 2.10-2.01 (m, 2H), 1.94-1.83 (m, 1H), 1.85-1.67 (m, 2H), 1.64-1.47 (m, 1H), 1.38-1.31 (m, 1H), 0.88 (d, J=6.8 Hz, 3H), 0.85 (d, J=6.8 Hz, 3H). LC/MS: Eluent system A (retention time: 4.65 min); ESI-MS: 411 [M+H]⁺.

Compound 2

Synthesis of (2S)—N-{(1S)-1-cyano-2-[(3S)-2-oxopiperidin-3-yl]ethyl}-2-(3,3-dimethyl-2,5-dioxopyrrolidin-1-yl)-4-methylpentanamide, 2

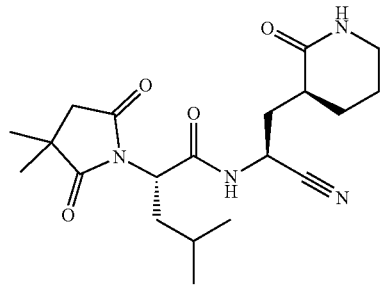

Compound 2 was synthesized as in Scheme 5.

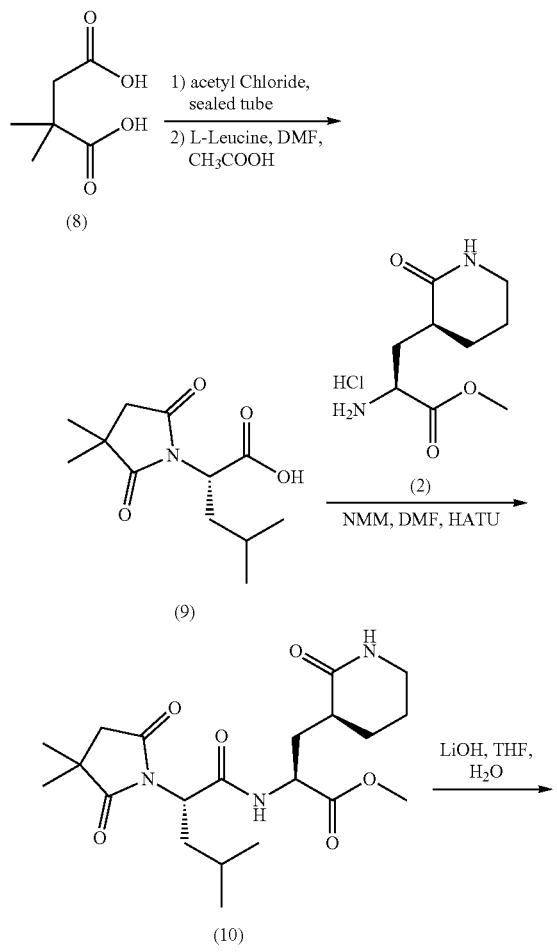

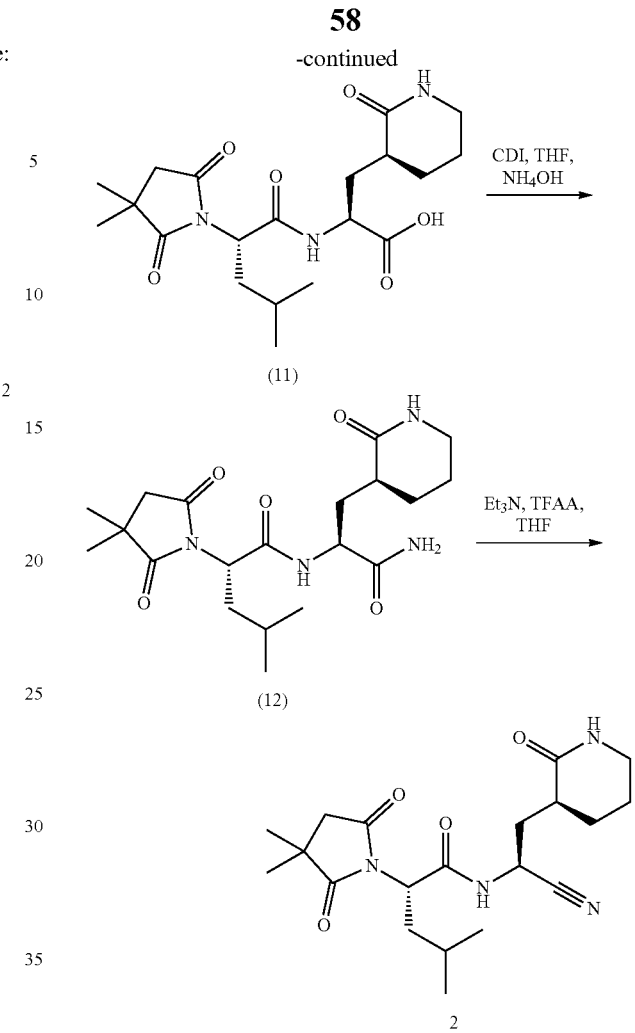

Preparation of (2S)-2-(3,3-dimethyl-2,5-dioxopyrrolidin-1-yl)-4-methylpentanoic acid, (9). A mixture of 2,2-dimethylbutanedioic acid (8) (292 mg, 2.00 mmol) and acetyl chloride (2 mL) in a sealed tube was heated overnight at 60° C., after which it was concentrated under reduced pressure. The residue was dissolved in DMF (2 mL), L-leucine (263 mg, 2.00 mmol) and acetic acid was added. The mixture was irradiated in a microwave reactor for 3 h at 120° C., after which it was concentrated under reduced pressure. The product was purified by column chromatography on silica gel with a gradient of 50 to 100% EtOAc in hexanes, which generated (9) (256 mg, 55% yield) as a gum. LC/MS: Eluent system B (retention time: 4.39 min); ESI-MS: 244 [M+H]⁺.

Preparation of methyl N-[(2S)-2-(3,3-dimethyl-2,5-dioxopyrrolidin-1-yl)-4-methylpentanoyl]-3-[(3S)-2-oxopiperidin-3-yl]-L-alaninate, (10). The procedure for (5) in Scheme 4 was followed with (2S)-2-(3,3-dimethyl-2,5-dioxopyrrolidin-1-yl)-4-methylpentanoic acid (9) (120 mg, 0.497 mmol), 3-[(3S)-2-oxopiperidin-3-yl]-L-alaninate-hydrogen chloride (2) (118 mg, 0.598 mmol), HATU (285 mg, 0.750 mmol), NMM (253 mg, 2.50 mmol) and DMF (3 mL). The product was purified by column chromatography on silica gel with a gradient of 50 to 100% EtOAc in hexanes, which generated (10) (139.8 mg, 66% yield) as a gum. LC/MS: Eluent system A (retention time: 3.36 min); ESI-MS: 424 [M+H]⁺.

Preparation of N-[(2S)-2-(3,3-dimethyl-2,5-dioxopyrrolidin-1-yl)-4-methylpentanoyl]-3-[(3S)-2-oxopiperidin-3-yl]-

L-alanine, (11). The procedure for (6) in Scheme 4 was followed with N-[(2S)-2-(3,3-dimethyl-2,5-dioxopyrrolidin-1-yl)-4-methylpentanoyl]-3-[(3S)-2-oxopiperidin-3-yl]-L-alaninate (10) (140 mg, 0.331 mmol), LiOH (39.5 mg, 1.65 mmol, in 2 mL of H$_2$O) and THF (mL), which generated upon concentration (11) (82 mg, 60% yield) as a gum. LC/MS: Eluent system A (retention time: 0.84 min); ESI-MS: 428 [M+H+H$_2$O]$^+$.

Preparation of (2S)—N-{(2S)-1-amino-1-oxo-3-[(3S)-2-oxopiperidin-3-yl]propan-2-yl}-2-(3,3-dimethyl-2,5-dioxopyrrolidin-1-yl)-4-methylpentanamide, (12). The procedure for (7) in Scheme 4 was followed with N-[(2S)-2-(3,3-dimethyl-2,5-dioxopyrrolidin-1-yl)-4-methylpentanoyl]-3-[(3S)-2-oxopiperidin-3-yl]-L-alanine (11) (82 mg, 0.20 mmol), carbonyldiimidazole (CDI) (65 mg, 0.40 mmol), aqueous ammonium hydroxide solution (28-30%) (0.20 mL, 4.8 mmol) and THF (5 mL). The product was purified by column chromatography on silica gel with a gradient of 0% to 10% MeOH in CHCl$_3$, which generated (12) (52 mg, 63% yield) as a gum. LC/MS: Eluent system A (retention time: 2.25 min); ESI-MS: 409 [M+H]$^+$.

Preparation of (2S)—N-{(1S)-1-cyano-2-[(3S)-2-oxopiperidin-3-yl]ethyl}-2-(3,3-dimethyl-2,5-dioxopyrrolidin-1-yl)-4-methylpentanamide, 2. The procedure for 1 in Scheme 4 was followed with (12) (52 mg, 0.13 mmol), Et$_3$N (39 mg, 0.38 mmol), trifluoroacetic anhydride (TFAA) (54 mg, 0.26 mmol) and THF (5 mL). The product was purified by column chromatography on silica gel with a gradient of 0% to 10% MeOH in CHCl$_3$, which generated 2 (5 mg, 10% yield) as a gum. LC/MS: Eluent system A (retention time: 3.05 min); ESI-MS: 391 [M+H]$^+$.

Compound 5

Synthesis of (2S)—N-{(1S)-1-cyano-2-[(3S)-2-oxopiperidin-3-yl]ethyl}-2-[(3R)-2,5-dioxo-3-phenylpyrrolidin-1-yl]-4-methylpentanamide, 5

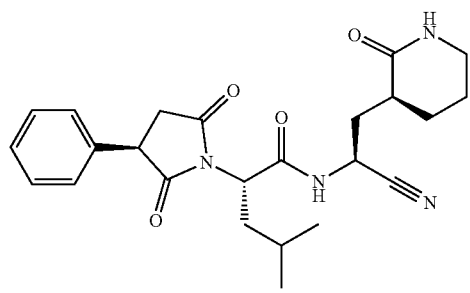

(5)

Compound 5 was synthesized as in Scheme 6.

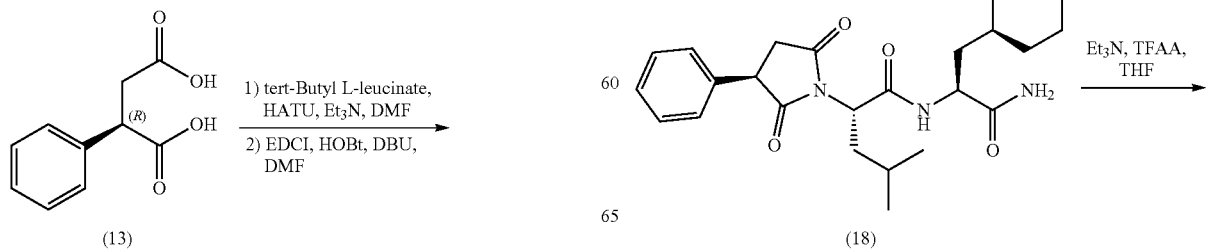

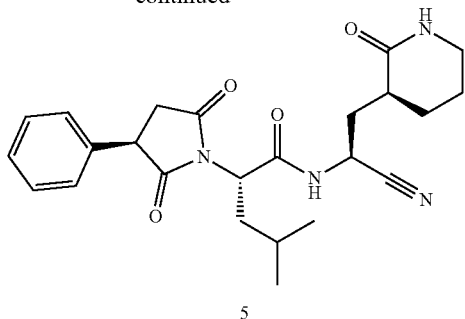

Preparation of tert-butyl (2S)-2-[(3R)-2,5-dioxo-3-phenylpyrrolidin-1-yl]-4-methylpentanoate, (14). To a solution of (2R)-2-phenylbutanedioic acid (13) (194 mg, 1.00 mmol) in DMF (10 mL) was added HATU (570 mg, 1.50 mmol) followed by Et₃N (506 mg, 5.00 mmol), then after 15 min, tert-butyl leucinate (224 mg, 1.01 mmol) was added. After 1 h, the mixture was diluted with DCM (100 mL), washed with water (25 mL), dried over MgSO₄, filtered and concentrated under reduced pressure. The resulting residue was mixed with EDCI (213 mg, 1.11 mmol), HOBt (150 mg, 1.11 mmol), DBU (563 mg, 3.70 mmol) and DMF, then heated at 50° C. for 3 h. It was then cooled to room temperature, 1N HCl (10 mL) was added and the resulting mixture was extracted with DCM (3×50 mL). The combined organic layer was concentrated and the product was purified by column chromatography on silica gel with a gradient of 0% to 10% MeOH in CHCl₃, which generated (14) (162 mg, 63% yield) as a gum. LC/MS: Eluent system A (retention time: 6.60 min); ESI-MS: 346 [M+H]⁺.

Preparation of (2S)-2-[(3R)-2,5-dioxo-3-phenylpyrrolidin-1-yl]-4-methylpentanoic acid, (15). To a solution of (14) (162 mg, 0.47 mmol) in DCM (5 mL) was added TFA (2 mL) slowly. After 3 h the mixture was concentrated, which provided (15) (109 mg, 80% yield). LC/MS: Eluent system A (retention time: 4.56 min); ESI-MS: 290 [M+H]⁺, 288 [M–H]⁻.

Preparation of methyl N-{(2S)-2-[(3R)-2,5-dioxo-3-phenylpyrrolidin-1-yl]-4-methylpentanoyl}-3-[(3S)-2-oxopiperidin-3-yl]-L-alaninate, (16). The procedure for (5) in Scheme 4 was followed with (2S)-2-[(3R)-2,5-dioxo-3-phenylpyrrolidin-1-yl]-4-methylpentanoic acid (15) (109 mg, 0.377 mmol), 3-[(3S)-2-oxopiperidin-3-yl]-L-alaninate, hydrogen chloride salt (2) (110 mg, 0.465 mmol), HATU (177 mg, 0.465 mmol), NMM 191 mg, (1.89 mmol) and DMF (5 mL). The product was purified by column chromatography on silica gel with a gradient of 0 to 10% MeOH in CHCl₃, which generated (16) (81.8 mg, 46% yield) as a gum. LC/MS: Eluent system A (retention time: 4.69 min, 4.89 min); ESI-MS: 472 [M+H]⁺.

Preparation of N-{(2S)-2-[(3R)-2,5-dioxo-3-phenylpyrrolidin-1-yl]-4-methylpentanoyl}-3-[(3S)-2-oxopiperidin-3-yl]-L-alanine, (17). The procedure for (6) in Scheme 4 was followed with methyl N-{(2S)-2-[(3R)-2,5-dioxo-3-phenylpyrrolidin-1-yl]-4-methylpentanoyl}-3-[(3S)-2-oxopiperidin-3-yl]-L-alaninate (16) (81.8 mg, 0.174 mmol), LiOH (21 mg, 0.87 mmol in 1 mL of H₂O) and THF, which generated upon concentration (17) (63.1 mg, 79% yield) as a gum. LC/MS: Eluent system A (retention time: 3.46 min); ESI-MS: 476 [M+H+H₂O]⁺.

Preparation of (2S)—N-{(2S)-1-amino-1-oxo-3-[(3S)-2-oxopiperidin-3-yl]propan-2-yl}-2-[(3R)-2,5-dioxo-3-phenylpyrrolidin-1-yl]-4-methylpentanamide, (18). The procedure for (7) in Scheme 4 was followed with N-{(2S)-2-[(3R)-2,5-dioxo-3-phenylpyrrolidin-1-yl]-4-methylpentanoyl}-3-[(3S)-2-oxopiperidin-3-yl]-L-alanine (17) (63.1 mg 0.138 mmol), carbonyldiimidazole (CDI) (44.8 mg, 0.276 mmol), aqueous ammonium hydroxide solution (28-30%) (0.20 mL, 4.8 mmol) and THF (10 mL). The product was purified by column chromatography on silica gel with a gradient of 0% to 10% MeOH in CHCl₃, which generated (18) as a gum. LC/MS: Eluent system A (retention time: 3.97 min); ESI-MS: 457 [M+H]⁺.

Preparation of (2S)—N-{(1S)-1-cyano-2-[(3S)-2-oxopiperidin-3-yl]ethyl}-2-[(3R)-2,5-dioxo-3-phenylpyrrolidin-1-yl]-4-methylpentanamide, 5. The procedure for 1 in Scheme 4 was followed with (2S)—N-{(2S)-1-amino-1-oxo-3-[(3S)-2-oxopiperidin-3-yl]propan-2-yl}-2-[(3R)-2,5-dioxo-3-phenylpyrrolidin-1-yl]-4-methylpentanamide (18) (48 mg, 0.11 mmol), Et₃N (32.0 mg, 0.316 mmol), trifluoroacetic anhydride (TFAA) (44 mg, 0.21 mmol) and THF (5 mL), which generated 5 (12 mg) as a gum. LC/MS: Eluent system A (retention time: 4.55 min); ESI-MS: 437 [M–H]⁻.

Compound 7

Synthesis of tert-butyl {1-[(2S)-1-({(1S)-1-cyano-2-[(3S)-2-oxopiperidin-3-yl]ethyl}amino)-4-methyl-1-oxopentan-2-yl]-2-oxo-1,2-dihydropyridin-3-yl}carbamate, 7

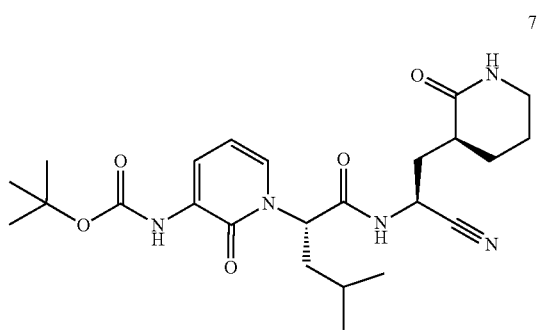 [SMILES: CC(C)C[C@@H](C(=O)N[C@H](C#N)C[C@@H]1CCCNC1=O)n1cccc(NC(=O)OC(C)(C)C)c1=O]

Compound 7 was synthesized as in scheme 7.

Scheme 7

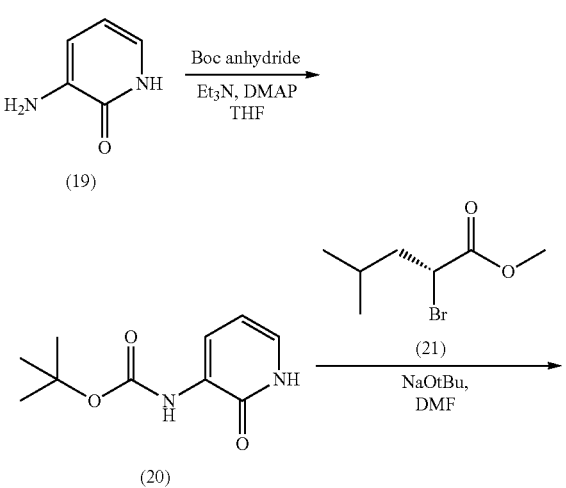

-continued

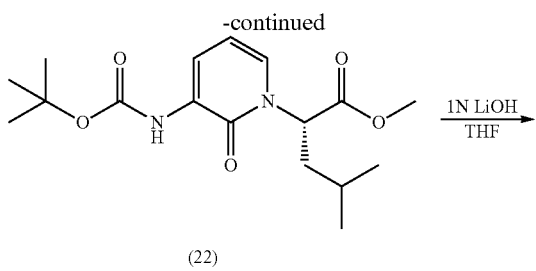

(22)

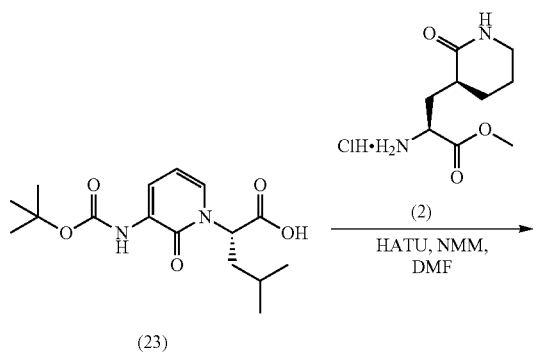

(23)

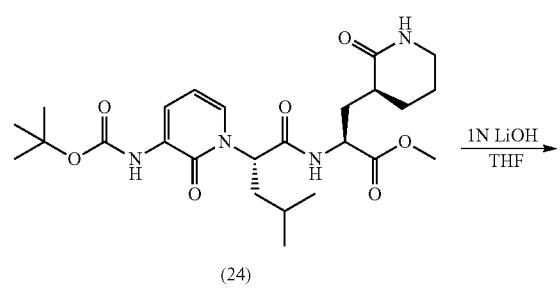

(24)

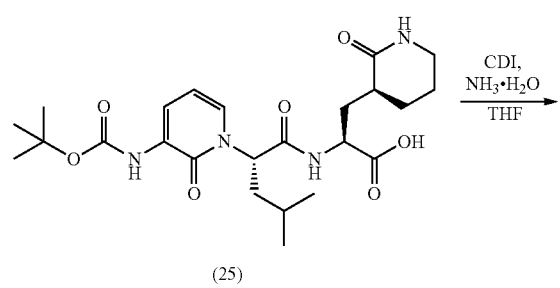

(25)

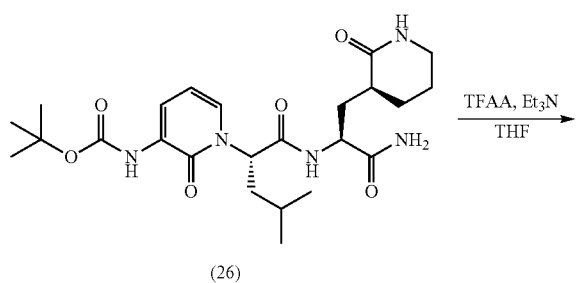

(26)

-continued

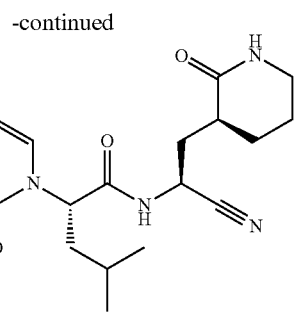

7

Preparation of tert-butyl (2-oxo-1,2-dihydropyridin-3-yl) carbamate, (20). To a solution of 3-aminopyridin-2(1H)-one (19) (750 mg, 6.81 mmol) in THF (15 mL) was added Boc anhydride (1.64 g, 7.49 mmol), triethylamine (1.42 mL, 10.2 mol), and DMAP (41.6 mg, 0.340 mmol). After overnight, water (25 mL) was added and the mixture was extracted with EtOAc (3×25 mL). The combined organic layer was washed with brine (1×25 mL) and dried over anhydrous $Na_2SO_4$, filtered, and concentrated under reduced pressure. The residue was dissolved in $CHCl_3$ (5 mL) and loaded on silicycle 40 g silica gel column. The produce was purified by Biotage® using a gradient of EtOAc in hexanes 0 to 30% as an eluent followed by recrystallization (acetone) generated (20) (960 mg, 67% yield) as a white solid. LC/MS: Eluent system C (retention time: 6.73 min); ESI-MS: 210 [M+H]$^+$.

Preparation of methyl (2S)-2-{3-[(tert-butoxycarbonyl)amino]-2-oxopyridin-1(2H)-yl}-4-methylpentanoate, (22). To a solution of tert-butyl (2-oxo-1,2-dihydropyridin-3-yl) carbamate (20) (201 mg, 0.956 mmol) in DMF (10 mL) was cooled in an ice-bath was added sodium tert-butoxide (175.5 mg, 1.910 mmol). After 30 min, a solution of methyl (2R)-2-bromo-4-methylpentanoate (21) (200 mg, 0.956 mmol) in DMF (2 mL) [prepared using a similar procedure to Moumne, R. et al Journal of Organic Chemistry, 2006, volume 71, pg 3331-3334 and Bursavich, M. G. and coinventors in WO2019/200202] was added over 15 min. The ice-bath was then removed. After overnight at ambient temperature, chilled water (20 mL) was added and the resulting mixture was extracted with EtOAc (3×20 mL). The combined layer was washed with brine (1×20 mL), dried over anhydrous $Na_2SO_4$, filtered and concentrated under pressure. The product was purified by Biotage® (silicycle 25 g silica gel column) with a gradient of 0 to 100% EtOAc in hexanes, which afforded (22) (217 mg, 67% yield) as an off-white solid. LC/MS: Eluent system B (retention time: 8.81 min); ESI-MS: 339 [M+H]$^+$.

Preparation of (2S)-2-{3-[(tert-butoxycarbonyl)amino]-2-oxopyridin-1(2H)-yl}-4-methylpentanoic acid, (23). A solution of methyl (2S)-2-{3-[(tert-butoxycarbonyl)amino]-2-oxopyridin-1(2H)-yl}-4-methylpentanoate (22) (217 mg, 0.641 mmol) in THF (10 mL) was cooled in an ice-bath and 1N LiOH aqueous solution (5 mL) was then added. After 1 h, the pH of the reaction mixture was adjusting to ~6 by adding 1N HCl aqueous solution. The two layers were separated and the aqueous layer was extracted with EtOAc (3×20 mL). The combined organic layer was washed with brine (1×20 mL), dried over anhydrous $Na_2SO_4$, filtered, and concentrated and dried under reduced pressure, which generated (23) as an off-white solid (208 mg). This material was used as such in the next step without further purification. LC/MS: Eluent system A (retention time: 5.91 min); ESI-MS: 325 [M+H]$^+$, 323 [M−H]$^−$.

Preparation of methyl N-[(2S)-2-{3-[(tert-butoxycarbonyl)amino]-2-oxopyridin-1(2H)-yl}-4-methylpentanoyl]-3-[(3S)-2-oxopiperidin-3-yl]-L-alaninate, (24). To a solution of (2S)-2-{3-[(tert-butoxycarbonyl)amino]-2-oxopyridin-1(2H)-yl}-4-methylpentanoic acid (23) (208 mg, 0.642 mmol) and methyl 3-[(3S)-2-oxopiperidin-3-yl]-L-alaninate hydrochloride salt (2) (160 mg, 0.674 mmol) in anhydrous DMF (10 mL) cooled in an ice-bath was added HATU (269 mg, 0.707 mmol) followed by NMM (0.212 mL, 1.93 mmol) dropwise. After 1 h, chilled water (25 mL) was added and the resulting mixture was extracted with EtOAc (3×25 mL). The combined organic layer was washed with brine solution (1×25 mL), dried over anhydrous $Na_2SO_4$, filtered, and concentrated under reduced pressure. The product was purified by Biotage® (Silicyle 25 g silica gel column) with a gradient of 0 to 100% EtOAc in hexanes, which generated (24) (246 mg, 75% yield) as a white solid. LC/MS: Eluent system A (retention time: 6.05 min); ESI-MS: 507 $[M+H]^+$.

Preparation of N-[(2S)-2-{3-[(tert-butoxycarbonyl)amino]-2-oxopyridin-1(2H)-yl}-4-methylpen-tanoyl]-3-[(3S)-2-oxopiperidin-3-yl]-L-alanine, (25). A solution of methyl N-[(2S)-2-{3-[(tert-butoxycarbonyl)amino]-2-oxopyridin-1(2H)-yl}-4-methylpentanoyl]-3-[(3S)-2-oxopiperidin-3-yl]-L-alaninate (24) (246 mg, 0.485 mmol) in THF (10 mL) was cooled in an ice-bath and 1N LiOH aqueous solution (5 mL) was added. After 1 h, the pH of the reaction mixture was adjusting to ~6 by adding 1N HCl aqueous solution. The two layers were separated and the aqueous layer was extracted with EtOAc (3×25 mL). The combined organic layer was washed with brine (1×25 mL), dried over anhydrous $Na_2SO_4$, filtered, and concentrated and dried under reduced pressure, which generated (25) (227 mg) as an off-white solid. This material was used as such in the next step without further purification. LC/MS: Eluent system B (retention time: 8.25 min); ESI-MS: 493 $[M+H]^+$, 491 $[M-H]^-$.

Preparation of tert-butyl {1-[(2S)-1-({(2S)-1-amino-1-oxo-3-[(3S)-2-oxopiperidin-3-yl]propan-2-yl}amino)-4-methyl-1-oxopentan-2-yl]-2-oxo-1,2-dihydropyridin-3-yl}carbamate, (26). To a solution of N-[(2S)-2-{3-[(tert-butoxycarbonyl)amino]-2-oxopyridin-1(2H)-yl}-4-methylpentanoyl]-3-[(3S)-2-oxopiperidin-3-yl]-L-alanine (25) (227 mg, 0.461 mmol) in anhydrous THF (10 mL) was added CDI (112 mg, 0.688 mmol). After 30 min at room temperature, $NH_3$ (aq., 28%, 0.280 mL, 2.31 mmol) was added. After 1 h, quenched with water (25 mL) and extracted with EtOAc (3×50 mL). The combined organic phase was washed with brine (1×50 mL), dried over anhydrous $Na_2SO_4$, filtered, and concentrated under reduced pressure. Purification was accomplished by Biotage® (Silicycle 25 g silica gel column) with a gradient of 0 to 2% MeOH in $CHCl_3$, which generated the (26) (154 mg, 70% yield) as a white solid. LC/MS: Eluent system A (retention time: 5.47 min); ESI-MS: 492 $[M+H]^+$.

Preparation of tert-butyl {1-[(2S)-1-({(1S)-1-cyano-2-[(3S)-2-oxopiperidin-3-yl]ethyl}amino)-4-methyl-1-oxo-pentan-2-yl]-2-oxo-1,2-dihydropyridin-3-yl}carbamate, 7. To tert-butyl {1-[(2S)-1-({(2S)-1-amino-1-oxo-3-[(3S)-2-oxopiperidin-3-yl]propan-2-yl}amino)-4-methyl-1-oxopentan-2-yl]-2-oxo-1,2-dihydropyridin-3-yl}carbamate (26) (154 mg, 0.314 mmol) in anhydrous THF (10 mL) cooled in an ice bath was added $Et_3N$ (0.13 mL, 0.94 mmol), followed by TFAA (0.087 mL, 0.63 mmol) dropwise. After 30 min, water (10 mL) was added and the two layers were separated. The aqueous layer was extracted with EtOAc (3×50 mL). The combined organic layer was washed with brine (1×50 mL), dried over anhydrous $Na_2SO_4$, filtered, and concentrated under reduced pressure. The product was purified by Biotage® (Silicyle 4×12 g silica gel columns) with a gradient of 0 to 100% EtOAc in hexanes, which generated 7 (18.5 mg, 12% yield) as a white solid. $^1$H NMR (600 MHz, DMSO-$d_6$) δ 9.23-9.18 (m, 1H), 7.82-7.78 (m, 1H), 7.77-7.74 (m, 1H), 7.57-7.51 (m, 1H), 7.41-7.37 (m, 1H), 6.32 (t, J=7.2 Hz, 1H), 5.57-5.51 (m, 1H), 5.02-4.93 (m, 1H), 3.14-3.03 (m, 2H), 2.33-2.11 (m, 2H), 2.02-1.95 (m, 1H), 1.88-1.68 (m, 4H), 1.64-1.49 (m, 1H), 1.46 (s, 9H), 1.44-1.34 (m, 1H), 1.31-1.21 (m, 1H), 0.89-0.87 (m, 3H), 0.87-0.84 (m, 3H). LC/MS: Eluent system A (retention time: 5.91 min); ESI-MS: 474 $[M+H]^+$.

Compound 8

Synthesis of (2S)—N-{(1S)-1-cyano-2-[(3S)-2-oxopiperidin-3-yl]ethyl}-4-methyl-2-(2-methyl-4-oxo-3,4-dihydro-5H-imidazo[4,5-c]pyridin-yl)pentanamide, 8

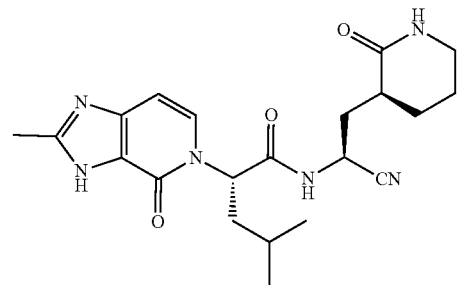

Compound 8 was synthesized as in Scheme 8.

Scheme 8

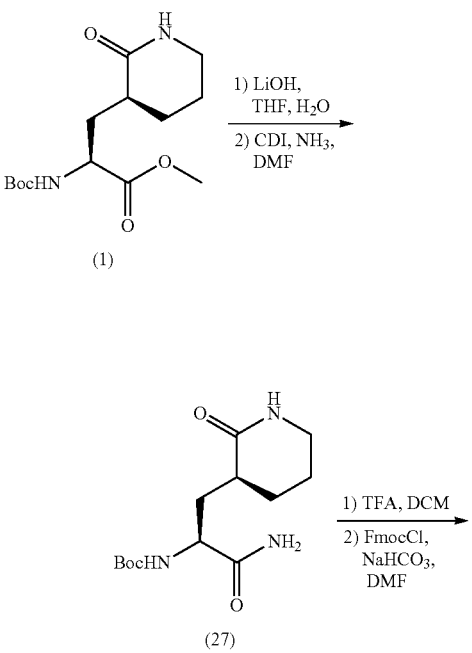

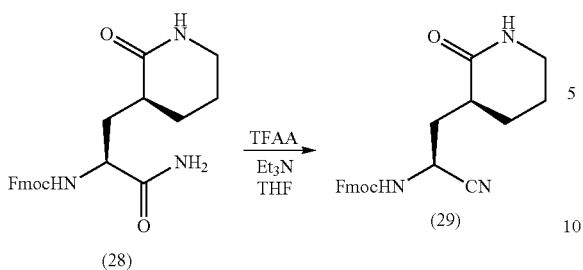

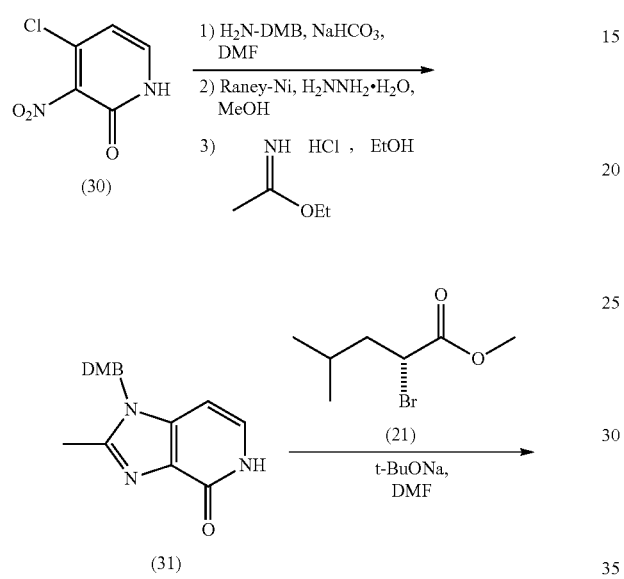

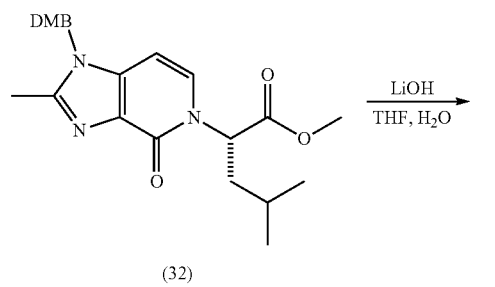

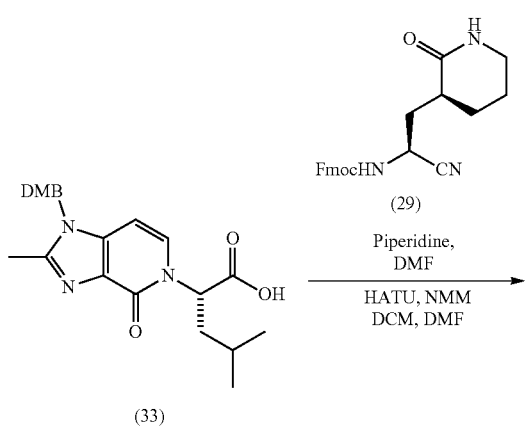

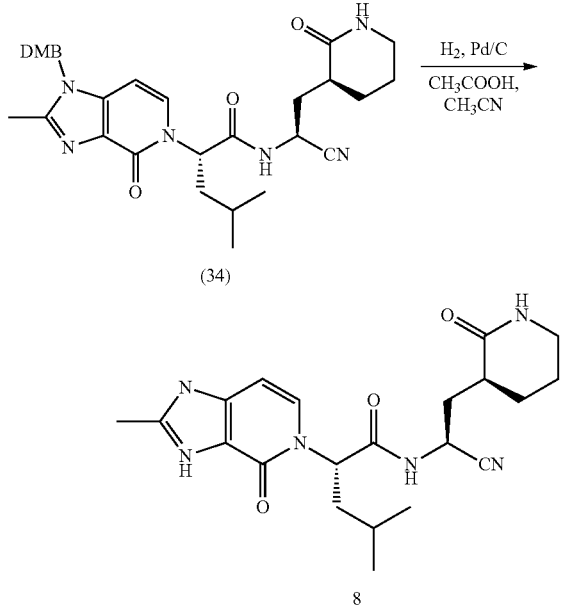

Preparation of tert-butyl {(2S)-1-amino-1-oxo-3-[(3S)-2-oxopiperidin-3-yl]propan-2-yl}carbamate, (27). Saponification of methyl N-(tert-butoxycarbonyl)-3-[(3S)-2-oxopiperidin-3-yl]-L-alaninate (1) (335 mg, 1.12 mmol) was performed as reported for (6). After 1 h in an icebath the reaction mixture became clear, the pH was adjusted to 4.0 with 1M aqueous HCl and the mixture was extracted with ethyl acetate (3×20 mL) providing 197 mg of a clear oil. Following the procedure for (7) with CDI (354 mg, 2.18 mmol) and aqueous ammonia (0.7 mL, ~10.1 mmol) followed by purification of the product by column chromatography on silica with a gradient of 0 to 20% of methanol in ethyl acetate provided (27) (102 mg, 32% yield over the two steps) as colorless oil. LC/MS: Eluent system C (retention time: 5.15 min); ESI-MS: 286 [M+H]$^+$.

Preparation of (9H-fluoren-9-yl)methyl {(2S)-1-amino-1-oxo-3-[(3S)-2-oxopiperidin-3-yl]propan-2-yl}carbamate, (28). To a solution of tert-butyl {(2S)-1-amino-1-oxo-3-[(3S)-2-oxopiperidin-3-yl]propan-2-yl}carbamate (27) (88.1 mg, 0.309 mmol) in DCM (3 mL) cooled in an icebath was added with TFA (1.0 mL). After 2 h, the mixture was concentrated under reduced pressure and the resulting residue was dissolved in 1,4-dioxane (15 mL) and a solution of sodium bicarbonate (2.18 g, 25.9 mmol) in water (20 mL) was added slowly, followed by 9-fluorenylmethyloxycarbonyl chloride (310 mg, 1.20 mmol) and another portion of 1,4-dioxane (15 mL). The mixture was sonicated at room temperature for 10 minutes, then it was diluted with water (10 mL) and extracted with ethyl acetate (3×25 mL). The combined organic layer was washed with brine (15 mL), dried with anhydrous sodium sulfate, filtered and concentrated under reduced pressure. The product was purified by column chromatography on silica with a gradient of 0 to 12% methanol in chloroform, providing (28) (124 mg, quantitative yield) as off-white solid. LC/MS: Eluent system B (retention time: 6.55 min); ESI-MS: 408 [M+H]$^+$.

Preparation of (9H-fluoren-9-yl)methyl {(1S)-1-cyano-2-[(3S)-2-oxopiperidin-3-yl]ethyl}carbamate, (29). Conversion of the primary amide (28) (124 mg, 0.304 mmol) into a corresponding nitrile was performed as reported for 1 with triethylamine (255 mg, 2.52 mmol) and TFAA (389 mg, 1.85 mmol). Purification by column chromatography on silica with 100% ethyl acetate provided (29) (103 mg, 87% yield) as colorless gum. LC/MS: Eluent system B (retention time: 8.07 min); ESI-MS: 390 [M+H]⁺.

Preparation of 1-[(3,4-dimethoxyphenyl)methyl]-2-methyl-1,5-dihydro-4-imidazo[4,5-c]pyridin-4-one, (31). A mixture of 4-chloro-3-nitro-2(1H)-one (30) (502 mg, 2.88 mmol), 3,4-dimethoxybenzylamine (508 mg, 3.04 mmol) and sodium bicarbonate (498 mg, 5.93 mmol) in DMF (15 mL) was stirred at room temperature. After overnight, the mixture was filtered through a cotton plug, that was washed with methanol (20 mL) and the combined filtrate was concentrated under reduced pressure. The residue was suspended in methanol (20 mL) and added to a refluxing suspension of Raney nickel (0.90 g) in methanol (50 mL) that had been treated with hydrazine hydrate (2.68 g, 41.8-50.2 mmol). After refluxing for 1 h another portion of the Raney nickel (1.20 g) and hydrazine hydrate (1.18 g, 18.4-22.1 mmol) was added. After 15 min the reaction mixture was filtered through Celite*, the filter plug was washed with DMF (20 mL) followed by methanol (35 mL) and the combined filtrate was concentrated under reduced pressure to provide brown solid as a residue (618 mg). The residue was suspended in anhydrous ethanol (30 mL) and ethyl acetimidate hydrochloride (589 mg, 4.77 mmol) was added and the mixture was refluxed. After 36 h, the mixture was concentrated under reduced pressure and partitioned between ethyl acetate (50 mL) and aqueous sodium bicarbonate (35 mL). The separated aqueous layer was washed with ethyl acetate (2×50 mL). The combined organic layer was concentrated and the product purified by column chromatography on silica with a gradient of 0 to 20% of methanol in ethyl acetate provided (31) (146 mg, 17% yield over 3 steps) as a white solid. LC/MS: Eluent system C (retention time: 3.86 and 4.53 min); ESI-MS: 300 [M+H]⁺.

Preparation of methyl (2S)-2-{1-[(3,4-dimethoxybenzyl)methyl]-2-methyl-4-oxo-1,4-dihydro-5H-imidazo[4,5-c]pyridin-5-yl}-4-methylpentanoate, (32). To a stirred suspension of 1-[(3,4-dimethoxyphenyl)methyl]-2-methyl-1,5-dihydro-4-imidazo[4,5-c]pyridin-4-one (31) (146 mg, 0.488 mmol) in DMF (6 mL) was added sodium tert-butoxide (67.4 mg, 0.701 mmol) followed by (21) (635 mg, 3.04 mmol) 30 min later. After 3 h at room temperature another portion of (21) (327 mg, 1.57 mmol) and sodium tert-butoxide (21.9 mg, 0.228 mmol) were added and after an additional 30 min the reaction mixture was diluted with chloroform (40 mL) and washed with 5% aqueous sodium bicarbonate solution (15 mL) and brine (10 mL). The organic layer was dried with sodium sulfate, filtered and concentrated under reduced pressure. The product was purified by column chromatography on silica with a gradient of 0 to 7% of methanol in chloroform, which provided (32) (187 mg, 89% yield). LC/MS: Eluent system B (retention time: 6.37 min); ESI-MS: 428 [M+H]⁺.

Preparation of (2S)-2-{1-[(3,4-dimethoxybenzyl)methyl]-2-methyl-4-oxo-1,4-dihydro-5H-imidazo[4,5-c]pyridin-5-yl}-4-methylpentanoic acid, (33). To a solution of methyl (2S)-2-{1-[(3,4-dimethoxybenzyl)methyl]-2-methyl-4-oxo-1,4-dihydro-5H-imidazo[4,5-c]pyridin-5-yl}-4-methylpentanoate (32) (89.1 mg, 0.208 mmol) in THF (5 mL) cooled in an ice-bath was added aqueous 1M lithium hydroxide solution (3 mL) was added. After 90 min, the reaction mixture was acidified with 1M sodium bisulfate solution to pH 3 and concentrated under reduced pressure. Then toluene (5 mL) was added to the residue and the mixture was concentrated under reduced pressure. The residue was used at the next step without further purification. LC/MS: Eluent system B (retention time: 5.63 min); ESI-MS: 414 [M+H]⁺, 412 [M−H]⁻.

Preparation of N-{(1S)-1-cyano-2-[(3S)-2-oxopiperidin-3-yl]ethyl}-2-{1-[(3,4-dimethoxyphenyl)methyl]-2-methyl-4-oxo-5H-imidazo[4,5-c]pyridin-5-yl}-4-methylpentanamide, (34). A solution of (9H-fluoren-9-yl)methyl {(1S)-1-cyano-2-[(3S)-2-oxopiperidin-3-yl]ethyl}carbamate (29) (48.8 mg, 0.125 mmol) in DMF (4.0 mL) was mixed with piperidine (1.0 mL, 9.8 mmol). After 5 min, the mixture was concentrated under reduced pressure, and toluene (8 mL) was added to the residue and again the mixture was concentrated under reduced pressure. The residue was dissolved in 10:1 DCM-DMF mixture (5.5 mL), then a solution of (2S)-2-{1-[(3,4-dimethoxybenzyl)methyl]-2-methyl-4-oxo-1,4-dihydro-5H-imidazo[4,5-c]pyridin-5-yl}-4-methylpentanoic acid (33) {50% aliquote from the residue prepared from 0.208 mmol of (32)} in DMF (3 mL) was added and the mixture was cooled in the ice bath. After 10 minutes HATU (98.2 mg, 0.258 mmol) and NMM (73.1 mg, 0.723 mmol) were added. After 3 h in the icebath, the mixture was diluted with chloroform (15 mL) and washed with 5% aqueous sodium bicarbonate solution (10 mL), brine (10 mL), and the separated organic layer was poured onto petri dish and left overnight in the fume hood to evaporate. The product was purified by column chromatography on silica with a gradient 0 to 12% of methanol in ethyl acetate, which provided (34) (9.2 mg, 16% yield). LC/MS: Eluent system A (retention time: 3.10 min); ESI-MS: 563 [M+H]⁺.

Preparation of (2S)—N-{(1S)-1-cyano-2-[(3S)-2-oxopiperidin-3-yl]ethyl}-4-methyl-2-(2-methyl-4-oxo-3,4-dihydro-5H-imidazo[4,5-c]pyridin-yl)pentanamide, 8. An aliquot of N-{(1S)-1-cyano-2-[(3S)-2-oxopiperidin-3-yl]ethyl}-2-{1-[(3,4-dimethoxyphenyl)methyl]-2-methyl-4-oxo-5H-imidazo[4,5-c]pyridin-5-yl}-4-methylpentanamide (34) (0.5 mg, 0.0009 mmol) in acetonitrile (2 mL) was transferred into a round bottom flask, then acetic acid (5.6 mg, 0.093 mmol) was added, followed by 10% palladium on carbon (50% wet) (3.2 mg, 0.0015 mmol). The atmosphere in the flask was replaced with hydrogen using a hydrogen-filled balloon. After overnight LC/MS analysis revealed the complete consumption of (34) and the appearance of 8. LC/MS: Eluent system B (retention time: 5.31 min); ESI-MS: 413 [M+H]⁺.

Compound 20

Synthesis of (1R,2S,5S)—N-{(1S)-1-cyano-2[(3S)-2-oxopiperidin-3-yl]ethyl}-3-[N-(difluoroacetyl)-3-methyl-L-valyl]-6,6-dimethyl-3-azabicyclo[3.1.0]hexane-2-carboxamide

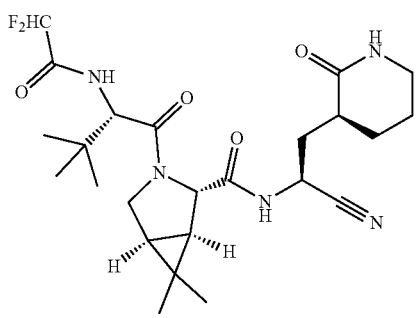

20

Compound 20 was synthesized as in Scheme 9.

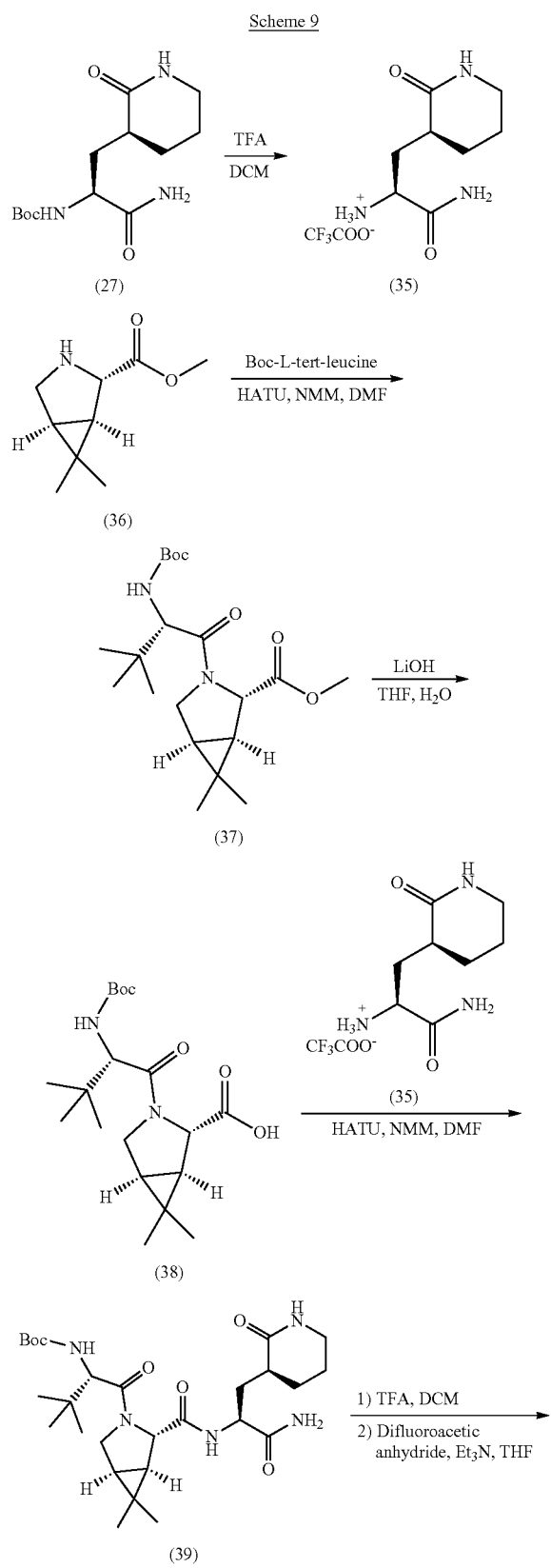

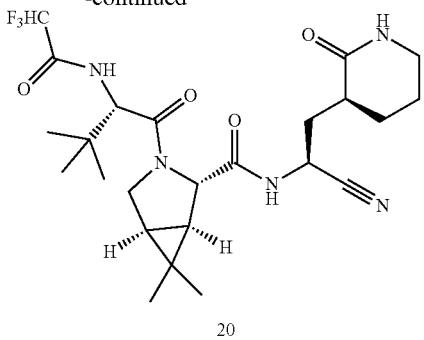

Preparation of (2S)-1-amino-1-oxo-3-[(3S)-2-oxopiperidin-3-yl]propan-2-aminium 2,2,2-trifluoroacetate, (35). To a solution of tert-butyl {(2S)-1-amino-1-oxo-3-[(3S)-2-oxopiperidin-3-yl]propan-2-yl}carbamate (27) (182 mg, 0.636 mmol) in DCM (5.0 mL) cooled in an ice bath was added with TFA (2.0 mL). After 3 h, the mixture was concentrated under reduced pressure. The resulting residue was dissolved in anhydrous DMF (3.0 mL) and used as is assuming 0.212M concentration of the target ammonium salt (35).

Preparation of methyl (1R,2S,5S)-3-[N-(tert-butoxycarbonyl)-3-methyl-L-valyl]-6,6-dimethyl-3-azabicyclo[3.1.0]hexane-2-carboxylate, (37). Following the procedure for (5) in Scheme 4 interaction of the (1R,2S,5S)-methyl 6,6-dimethyl-3-azabicyclo[3.1.0]hexane-2-carboxylate (36) (269 mg, 1.31 mmol) with the Boc-L-tert-leucine (502 mg, 2.17 mmol) in the presence of HATU (645 mg, 1.70 mmol) and NMM (890 mg, 8.80 mmol) in DMF (10.0 mL) after purification by column chromatography (eluted with the gradient of ethyl acetate in hexane from 0% to 100%) provided (37) (501 mg, quant. yield). LC/MS: Eluent system A (retention time: 6.56 min); ESI-MS: 383 [M+H]⁺.

Preparation of (1R,2S,5S)-3-[N-(tert-butoxycarbonyl)-3-methyl-L-valyl]-6,6-dimethyl-3-azabicyclo[3.1.0]hexane-2-carboxylic acid, (38). The procedure for (33) in Scheme 8 was followed using (1R,2S,5S)-3-[N-(tert-butoxycarbonyl)-3-methyl-L-valyl]-6,6-dimethyl-3-azabicyclo[3.1.0]hexane-2-carboxylate (37) (501 mg, 1.31 mmol) with 1M aqueous LiOH solution (2.5 mL) in THF (5.0 mL), provided (38) (521 mg, quantitative yield). LC/MS: Eluent system A (retention time: 6.07 min); ESI-MS: 369 [M+H]⁺, 367 [M−H]⁻.

Preparation of tert-butyl {(2S)-1-[(1R,2S,5S)-2-({(2S)-1-amino-1-oxo-3-[(3S)-2-oxopiperidin-3-yl]propan-2-yl}carbamoyl)-6,6-dimethyl-3-azabicyclo[3.1.0]hexan-3-yl]-3,3-dimethyl-1-oxobutan-2-yl}carbamate, (39). Following the procedure for (5) in Scheme 4 the reaction between the (1R,2S,5S)-3-[N-(tert-butoxycarbonyl)-3-methyl-L-valyl]-6,6-dimethyl-3-azabicyclo[3.1.0]hexane-2-carboxylic acid (38) (123.5 mg, 0.335 mmol) and (2S)-1-amino-1-oxo-3-[(3S)-2-oxopiperidin-3-yl]propan-2-aminium 2,2,2-trifluoroacetate (35) (1.5 mL of 0.212M solution in DMF, 0.318 mmol) in the presence of HATU (194 mg, 0.511 mmol) and NMM (190 mg, 1.88 mmol) in DMF (3.5 mL) provided after purification by column chromatography (eluted with the gradient of 0% to 20% methanol in DCM) (39) (32.1 mg, 19% yield). LC/MS: Eluent system A (retention time: 5.51 min); ESI-MS: 536 [M+H]⁺, 534 [M−H]⁻.

Preparation of (1R,2S,5S)—N-{(1S)-1-cyano-2-[(3S)-2-oxopiperidin-3-yl]ethyl}-3-[N-(difluoroacetyl)-3-methyl-L-valyl]-6,6-dimethyl-3-azabicyclo[3.1.0]hexane-2-carboxamide, 20. Following the Boc-deprotection performed as described for (35) in Scheme 9 using tert-butyl {(2S)-1-[(R,2S,5S)-2-({(2S)-1-amino-1-oxo-3-[(3S)-2-oxopiperidin-3-yl]propan-2-yl}carbamoyl)-6,6-dimethyl-3-azabicyclo[3.1.0]hexan-3-yl]-3,3-dimethyl-1-oxobutan-2-yl}carbamate (39) (32.1 mg, 0.0599 mmol) and TFA (1.5 mL) in DCM (4 mL), the residue obtained after evaporation of the volatile components under reduced pressure was dissolved in anhydrous THF (5.0 mL). The solution was cooled using the ice bath, triethylamine (462 mg, 4.56 mmol) was added followed by a slow addition of the solution of difluoroacetic anhydride (275 mg, 1.58 mmol) in THF (0.6 mL) over 30 seconds. After 15 minutes the reaction mixture was diluted with ethyl acetate (20 mL) and crushed ice (~5 g) was added, followed by a 5% sodium bicarbonate solution (10 mL). The organic layer was washed with brine (5 mL), dried with the anhydrous sodium sulfate, filtered and concentrated under reduced pressure. The product was purified by column chromatography on silica with a gradient 0 to 12% of methanol in DCM and then the resulting solid was triturated with ether providing 20 (8.9 mg, 30% yield over two steps) as a white powder. $^1$H NMR (600 MHz, DMSO-$d_6$) δ 8.98 (d, J=8.3 Hz, 1H), 8.81 (d, J=8.7 Hz, 1H), 7.49 (s, 1H), 6.27 (t, J=53.8 Hz, 1H), 5.00 (ddd, J=6.2, 8.3, 10.4 Hz, 1H), 4.38 (d, J=8.7 Hz, 1H), 4.16 (s, 1H), 3.90 (dd, J=5.5, 10.4 Hz, 1H), 3.73 (d, J=10.5 Hz, 1H), 3.14-3.03 (m, 2H), 2.37-2.18 (m, 2H), 1.89-1.81 (m, 1H), 1.78-1.64 (m, 2H), 1.61-1.51 (m, 2H), 1.41-1.32 (m, 1H), 1.28 (d, J=7.5 Hz, 1H), 1.03 (s, 3H), 0.96 (s, 9H), 0.84 (s, 3H). LC/MS: Eluent system A (retention time: 4.02 min); ESI-MS: 496 [M+H]$^+$, 494 [M−H]$^−$.

Compound 24

Synthesis of (1R,2S,5S)—N-{(1S)-1-cyano-2-[(3S)-2-oxo(6,6-$^2$H$_2$)piperidin-3-yl]ethyl}-3-[N-(difluoroacetyl)-3-methyl-L-valyl]-6,6-dimethyl-3-azabicyclo[3.1.0]hexane-2-carboxamide

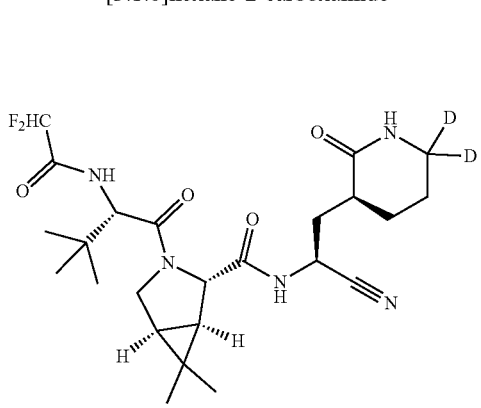

24

Compound 24 was synthesized as in Scheme 10.

Scheme 10

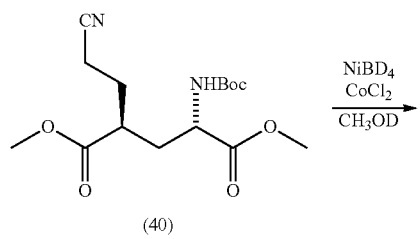

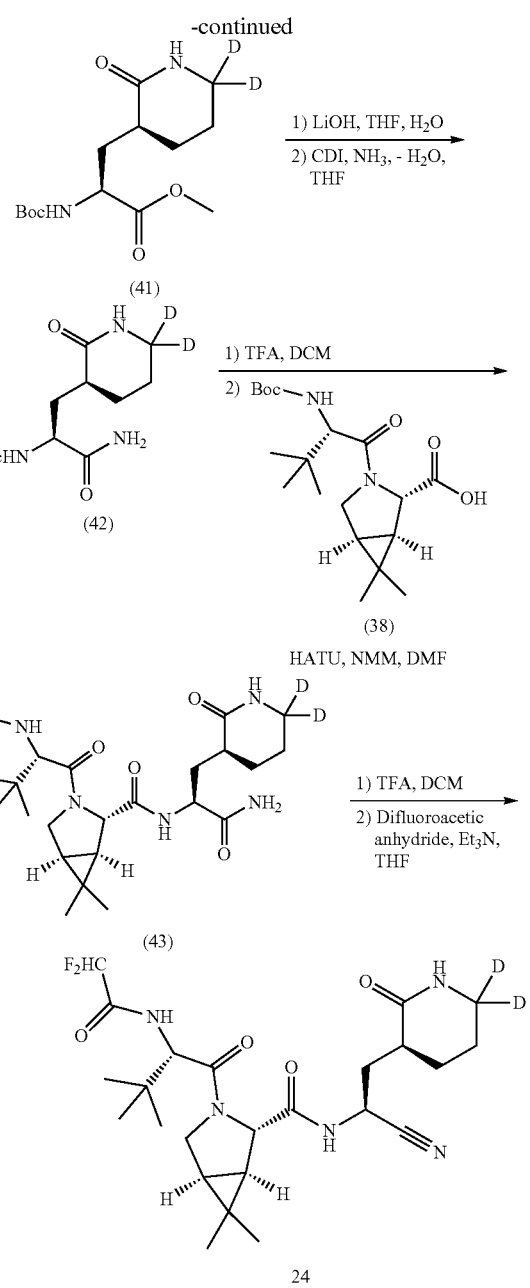

Preparation of methyl N-(tert-butoxycarbonyl)-3-[(3S)-2-oxo(6,6-$^2$H$_2$)piperidin-3-yl]-L-alaninate, (41). To the ice cold stirred solution of dimethyl (4S)—N-(tert-butoxycarbonyl)-4-(2-cyanoethyl)glutamate (40) (1.65 g, 5.02 mmol) [prepared according to Y. Zhai et al Journal of Medicinal Chemistry, year 2015, volume 58, pages 9414-9420] in methanol-OD (25 mL) containing anhydrous cobalt (II) chloride (394 mg, 3.03 mmol) and a few drops of D$_2$O (130 mg, 6.49 mmol), sodium borodeuteride (1150 mg, 27.5 mmol) was added in portions. After 2 hours the ice bath was removed and the mixture was left overnight. Then the reaction mixture was diluted with ethyl acetate (50 mL) and quenched with 1M sodium hydrosulfate solution (15 mL). Aqueous layer was extracted with ethyl acetate (2×15 mL) and the combined organic layer was rinsed with brine (20 mL), dried with anhydrous sodium sulfate, filtered and concentrated under reduced pressure. The product was purified by column chromatography on silica with a gradient 0 to 12% of methanol in DCM that provided (41) (976 mg, 64% yield) as a clear oil. LC/MS: Eluent system B (retention time: 4.83 min); ESI-MS: 303 [M+H]$^+$.

Preparation of tert-butyl {(2S)-1-amino-1-oxo-3-[(3S)-2-oxo(6,6-$^2$H$_2$)piperidin-3-yl]propan-2-yl}carbamate, (42). The sequence of the methyl ester saponification followed by a primary amide formation was performed with methyl N-(tert-butoxycarbonyl)-3-[(3S)-2-oxo(6,6-$^2$H$_2$)piperidin-3-yl]-L-alaninate (41) (297 mg, 0.982 mmol) following the procedure for (27) in Scheme 8, using 1M LiOH aqueous solution (3 mL) and THF (5 mL), CDI (726 mg, 4.48 mmol) and 14.8M ammonia solution (1.5 mL). The product was purified by column chromatography on silica with a gradient 0 to 20% of methanol in chloroform that provided (42) (87.1 mg, 31% yield over 2 steps). LC/MS: Eluent system B (retention time: 2.37 min); ESI-MS: 288 $[M+H]^+$.

Preparation of tert-butyl {(2S)-1-[(1R,2S,5S)-2-({(2S)-1-amino-1-oxo-3-[(3S)-2-oxo(6,6-$^2H_2$)piperidin-3-yl]propan-2-yl}carbamoyl)-6,6-dimethyl-3-azabicyclo[3.1.0]hexan-3-yl]-3,3-dimethyl-1-oxobutan-2-yl}carbamate, (43). A solution of tert-butyl {(2S)-1-amino-1-oxo-3-[(3S)-2-oxo(6,6-$^2H_2$)piperidin-3-yl]propan-2-yl}carbamate (42) (87.1 mg, 0.303 mmol) in DCM (5.0 mL) was treated with TFA (2 mL) following the procedure for (35) in Scheme 9. The residue obtained after concentration of the mixture was dissolved in DMF (5.0 mL) and treated with (1R,2S,5S)-3-[N-(tert-butoxycarbonyl)-3-methyl-L-valyl]-6,6-dimethyl-3-azabicyclo[3.1.0]hexane-2-carboxylic acid (38) (106.4 mg, 0.289 mmol) in the presence of HATU (274 mg, 0.720 mmol) and NMM (340 mg, 3.36 mmol) following the procedure for (5) in Scheme 4. Purification by a column chromatography on silica with a gradient 0 to 20% of methanol in DCM provided (43) (111 mg, 71% yield). LC/MS: Eluent system A (retention time: 5.44 min); ESI-MS: 538 $[M+H]^+$, 536 $[M-H]^-$.

Preparation of (1R,2S,5S)—N-{(1S)-1-cyano-2-[(3S)-2-oxo(6,6-$^2H_2$)piperidin-3-yl]ethyl}-3-[N-(difluoroacetyl)-3-methyl-L-valyl]-6,6-dimethyl-3-azabicyclo[3.1.0]hexane-2-carboxamide 24. The procedure was used for 20 in Scheme 9 with tert-butyl {(2S)-1-[(1R,2S,5S)-2-({(2S)-1-amino-1-oxo-3-[(3S)-2-oxo(6,6-$^2H_2$)piperidin-3-yl]propan-2-yl]carbamoyl)-6,6-dimethyl-3-azabicyclo[3.1.0]hexan-3-yl}-3,3-dimethyl-1-oxobutan-2-yl}carbamate (43) (55.5 mg, 0.103 mmol), TFA (1.0 mL) in DCM (3.0 mL) and triethylamine (420 mg, 4.15 mmol) and difluoroacetic anhydride (345 mg, 1.98 mmol) in THF (5.0 mL). Purification by a column chromatography on silica with a gradient 0 to 12% of methanol in DCM, followed by a trituration with ether provided 24 (23.9 mg, 47% yield) as white powder. $^1H$ NMR (600 MHz, DMSO-$d_6$) δ 8.99 (d, J=8.3 Hz, 1H), 8.82 (d, J=8.7 Hz, 1H), 7.47 (s, 1H), 6.28 (t, J=53.8 Hz, 1H), 5.01 (ddd, J=6.0, 8.2, 10.3 Hz, 1H), 4.39 (d, J=8.7 Hz, 1H), 4.16 (s, 1H), 3.90 (dd, J=5.5, 10.4 Hz, 1H), 3.73 (d, J=10.5 Hz, 1H), 2.37-2.20 (m, 2H), 1.93-1.81 (m, 1H), 1.80-1.63 (m, 2H), 1.61-1.46 (m, 2H), 1.46-1.32 (m, 1H), 1.29 (d, J=7.5 Hz, 1H), 1.03 (s, 3H), 0.97 (s, 9H), 0.84 (s, 3H). LC/MS: Eluent system A (retention time: 3.97 min); ESI-MS: 498 $[M+H]^+$, 496 $[M-H]^-$.

Example 2

In this example, methods and results from the development of compounds for use in treating Group IV RNA viruses are provided.

Methods and Materials

SARS-CoV-2 3-Chymotrypsin-Like Protease (3CLP) Expression and Purification

DNA encoding 3CLP from SARS-CoV-2 was obtained from BioBasic Inc. (Ontario, Canada) and codon optimized for expression in *Escherichia coli*. The gene was cloned into the pET SUMO (small ubiquitin-like modifier) expression vector (Invitrogen). Clones were sequenced to ensure that the SARS-CoV-2 3CLP protein was in frame with the His-tagged SUMO fusion protein. The resulting plasmid was transformed into *E. coli* BL21(DE3) and the *E. coli* transformant was grown in Luria Broth, Miller at 37° C. with shaking (220 rpm) to an OD600 of 0.6-0.7 using kanamycin (50 μg/mL) as selective pressure. Expression of the fusion protein was induced by the addition of 0.5 mM IPTG to the cell culture and the culture was grown for an additional 4-5 h at 37° C. Cells were harvested by centrifugation (6000 g for 10 min at 4° C.) and suspended in lysis buffer (20 mM Tris-HCl pH 7.8, 150 mM NaCl). Cells were lysed by sonication on ice and the lysate was centrifuged (17000 g for 10 min at 4° C.) to remove cellular debris. The supernatant was isolated and, after adding imidazole (5 mM), mixed with Ni-NTA resin (Qiagen). The mixture was loaded on a fritted column and allowed to flow by gravity at 4° C. The resin was washed with 10 column volumes (CV) of lysis buffer containing 20 mM imidazole. The fusion protein was eluted using 2 CV of lysis buffer containing increased concentrations of imidazole (40, 60, 80, 100, 200 and 500 mM). Eluted fractions were analyzed by SDS-PAGE and those that contained the fusion protein were pooled together, dialyzed against lysis buffer containing 1 mM DTT at 4° C. and concentrated using Amicon Ultra-15 filter (Millipore) with a MWCO of 10 kDa. The fusion protein was digested by His-tagged SUMO protease (McLab, South San Francisco, CA) at 4° C. for 1-2 h to remove the SUMO tag. The cleavage mixture was added to Ni-NTA resin and loaded on a fritted column. The flow through containing SARS-CoV-2 3CLP was collected and analyzed by SDS-PAGE. The SARS-CoV-2 3CLP protein was further purified using size exclusion chromatography (G-100, GE Healthcare, 1 ml/min flow rate, 4° C.) in 20 mM Tris, 20 mM NaCl, 1 mM DTT, pH 7.8. Immunoglobulin G, 166 kDa; bovine serum albumin, 67 kDa; ovalbumin, 43 kDa; and lysozyme, 15 kDa were used as calibration standards. Fractions containing the SARS-CoV-2 3CLP protein were pooled and concentrated using Amicon Ultra-15 filter with a MWCO of 10 kDa.

Mass Spectrometry of SARS-CoV-2 3CLP

The mass of the free SARS-CoV-2 3CLP was confirmed by HR-MALDI on a MALDI-TOF (Bruker Ultrafelxtreme, Bruker Daltronics, USA) and LC-MS on an ESI-TOF instrument (Agilent Technologies 6220, California, USA) using electrospray ionization.

Determination of Enzyme Inhibition in SARS-CoV-2 3-Chymotrypsin-Like Protease (3CLP) Assay Compounds described herein were screened for SARS-CoV-2 3CLP inhibition using a Fluorescence resonance energy transfer (FRET) assay at different compound concentrations. Examples of the resulting concentration response curves are shown in FIGS. 1A to 1C and examples of the determined 50 percent inhibition concentration ($IC_{50}$) are provided in TABLE 1.

Synthesis of FRET Peptide Substrate was performed following the procedures Vuong, W. et al *Nature Communications* 2020, 11 (https://doi.org/10.1038/s41467-020-18096-2).

Enzyme Kinetics of SARS-CoV-2 3CLP

A synthesized fluorescent substrate containing the cleavage site (indicated by the arrow, ↓) of SARS-CoV-2 3CLP (2-Abz-SVTLQ↓SG-Tyr(NO$_2$)—R—NH2) was used for the fluorescence resonance energy transfer (FRET)-based cleavage assay4. The protease reaction of SARS-CoV-2 3CLP towards fluorescent substrate was performed in activity buffer (20 mM Bis Tris, pH 7.8, 1 mM DTT) at 37° C. for 10 min. The final concentration of protease used in the assay was fixed at 80 nM and the concentrations of the substrate were varied from 0.1 to 500 µM. Reaction was started with the enzyme and the fluorescence signal of the Abz-SVTLQ peptide cleavage product was monitored at an emission wavelength of 420 nm with excitation at 320 nm, using an Flx800 fluorescence spectrophotometer (BioTek). Before kinetic calculations, it was verified that the proportionality between the fluorescence emitted and the amount of the substrate used in the assay was linear. The minimal concentration of the enzyme and time of reaction that gave a linear dependence of amount of generated product with time was chosen. Initial velocities in corresponding relative fluorescence units per unit of time (ARFU/s) were converted to the amount of the cleaved substrate per unit of time (M/s) by fitting to the calibration curve of free Aminobenzoyl-SVTLQ. All data are corrected for inner filter effects by an adopted literature protocol. In short, the fluorescence signal (RFU) at each substrate concentration was determined and defined as f(FRET). Then, 5 uL free Aminobenzoyl-SVTLQ at final 5 uM was added to each concentration and fluorescence was taken f(FRET+Aminobenzoyl-SVTLQ). Simultaneously, a reference reading was taken with the same free Aminobenzoyl-SVTLQ concentration and defined as f(ref). The inner-filter correction was obtained as:

$$\text{corr \%} = (f(\text{FRET}+\text{Aminobenzoyl-SVTLQ})-f(\text{FRET}))/f(\text{ref}) \times 100\%$$

The corrected initial velocity of the reaction was calculated as $$V = Vo/(\text{corr \%}).$$

Vo represents the initial velocity of each reaction.

Kinetic constants (vmax and Km) were derived by fitting the corrected initial velocity to the Michaelis-Menten equation, $v = v_{max} \times [S]/(K_m+[S])$ using GraphPad Prism 6.0 software. kcat/Km was calculated according to the equation, $k_{cat}/K_m = v_{max}/([E] \times K_m)$. Triplicate experiments were performed for each data point, and the average was determined.

Inhibition Parameters

Stock solutions of the compounds were prepared with DMSO. For the determination of the $IC_{50}$, 80 nM of SARS-CoV-2 3CLP was incubated with the compounds at various concentrations from 0 to 100 µM in 20 mM Bis-Tris, pH 7.8, 1 mM DTT at 37° C. for 10 min. The protease reaction was started by addition of 100 µM of the substrate. The GraphPad Prism 6.0 software (GraphPad) was used for the calculation of the $IC_{50}$ values. Results are shown in TABLE 1.

TABLE 1

SARS-CoV-2 3CLP activity

| Compound Number | 3CL Protease $IC_{50}$ (µM) |
|---|---|
| 1 | 8.5 |
| 2 | 10.7 |
| 5 | 6.9 |
| 7 | 0.90 |
| 20 | <0.1 |
| 24 | <0.1 |

Evaluation of In Vitro Inhibition Activity of Exemplary Compounds Against SARS-CoV-2

Compounds described herein are screened for inhibition of SARS-CoV-2 viral replication in an in vitro plaque reduction assay.

Determination of Inhibition and $EC_{50}$ by Plaque Assay

SARS-CoV-2/CANADA/VIDO 01/2020 was a kind gift from Darryl Falzarano (University of Saskatchewan). Vero (Female green monkey kidney) E6 cells were infected with an MOI of 0.0001 pfu/cell in infection medium consisting of DMEM supplemented with 1× non-essential amino acids (Gibco), 10 mM HEPES, 2% fetal bovine serum, 50 IU/mL penicillin, 50 IU/mL streptomycin with 10 µM or different doses of antiviral drugs. After 1 h, the infecting medium was removed and monolayers were overlaid with MEM supplemented with 10 mM HEPES and 1.2% Avicel RC-591 (DuPont). After 48 h, cells were fixed in 10% formaldehyde, and stained using 0.5% (w/v) crystal violet. Plaques were counted and for screening at 10 µdata compound that did not to reduce the plaque numbers by half were assign >10 PM. Results for compounds tested at multiple concentrations (10, 6, 3, 1, 0.6, 0.3, 0.1, 0.06, and 0.03 µM) were plotted as % inhibition vs the log 10[drug] using Prism (GraphPad). $EC_{50}$'s were determined using a non-linear regression analysis. Experiments were done in triplicate.

Measuring Cytotoxicity in A549 and Vero E6 Cells

Cell viability was measured using the CellTiter-Glo luminescent cell viability assay (Promega). Separately A549 (male human lung epithelial) cells and VeroE6 cells were seeded at 5×103 cells/well in 96-well plates and incubated overnight before treatment. Compounds were solubilized in DMSO and added to cells in an eight-point four-fold serial dilution (200 µM to 0.0122 µM). Cells were incubated in the presence of compounds for 24 hours before addition of the luminescence substrate and measurement of ATP activity according to manufacturer's instructions. The percentage of viable cells was calculated relative to cells treated with solvent alone (0.5% DMSO). Results are shown in TABLE 2.

TABLE 2

Inhibitor activity against SARS-CoV-2

| Compound Number | SARS-CoV-2 Antiviral $EC_{50}$ (µM) | Vero E6 and A549 $CC_{50}$ (µM) |
|---|---|---|
| 1 | >10 | |
| 2 | >10 | |
| 5 | >10 | |
| 7 | <10 | |
| 20 | <5 | >200 |
| 24 | <5 | >200 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula II:

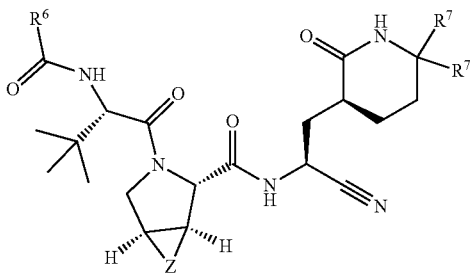

wherein:

R⁶ is selected from —CH₃ and —CHF₂;

each R⁷ is independently selected from —H, -D and —CH₃, or together two R⁷ and the carbon they are attached to form a cyclopropyl group; and Z is selected from —CH₂CH₂CH₂— and —C(CH₃)₂—;

or a pharmaceutically acceptable salt, solvate, or hydrate thereof.

2. The compound of claim 1, wherein the compound is selected from the following structures:

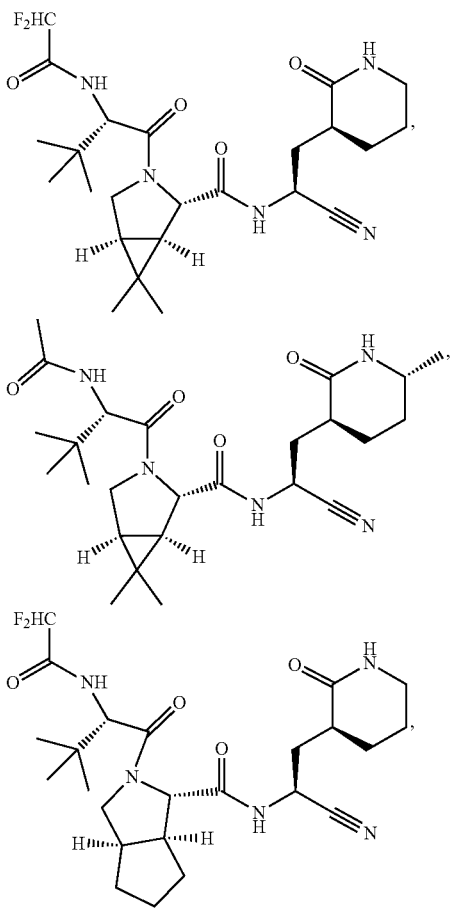

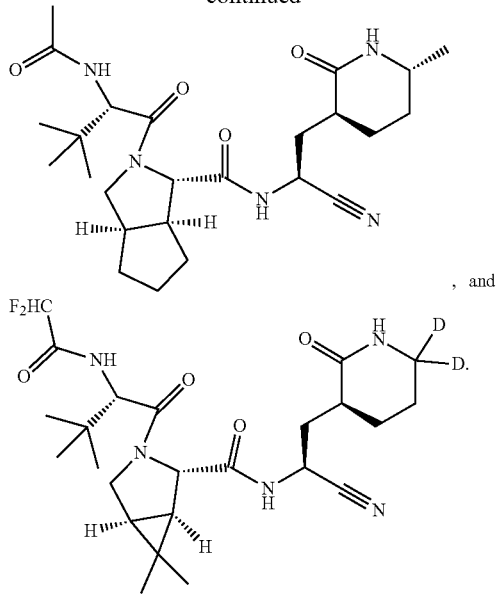

3. A method of inhibiting a Baltimore Group IV RNA virus in a cell infected with a Baltimore Group IV RNA virus, the method comprising contacting the cell with a compound of claim 1.

4. The method of claim 3, wherein the Baltimore Group IV RNA virus is selected from picornavirus, norovirus, and coronavirus.

5. The method of claim 4, wherein the Baltimore Group IV RNA virus is selected from enterovirus, rhinovirus, coxsackie virus, norovirus and coronavirus.

6. The method of claim 5, wherein the Baltimore Group IV RNA virus is coronavirus.

7. The method of claim 6, wherein the coronavirus is one that causes disease in mammals.

8. The method of claim 7, wherein the coronavirus causes disease in companion animals or livestock.

9. The method of claim 8, wherein the coronavirus is a feline coronavirus.

10. The method of claim 9, wherein the coronavirus is feline infectious peritonitis.

11. The method of claim 7, wherein the coronavirus is a human coronavirus.

12. The method of claim 11, wherein the coronavirus is selected from Severe Acute Respiratory Syndrome coronavirus 2 (SARS-CoV-2), Severe Acute Respiratory syndrome coronavirus 1 (SARS-CoV-1) and Middle Eastern Respiratory syndrome-related coronavirus (MERS-CoV).

13. A method of treating a Baltimore Group IV RNA virus infection in a mammal, the method comprising administering to the mammal an effective amount of a compound according to claim 1.

14. The method of claim 13, wherein the mammal is selected from a companion animal and livestock.

15. The method of claim 14, wherein the mammal is a feline.

16. The method of claim 13, wherein the mammal is a human.

17. The method of claim 13, wherein the Baltimore Group IV RNA virus is selected enterovirus, rhinovirus, coxsackie virus, norovirus and coronavirus.

18. The method of claim 17, wherein the Baltimore Group IV RNA virus is selected from norovirus, and coronavirus.

19. The method of claim 18, wherein the Baltimore Group IV RNA virus is human norovirus.

20. The method of claim 18, wherein the Baltimore Group IV RNA virus is a coronavirus that causes disease in mammals.

21. The method of claim 20, wherein the coronavirus is a feline coronavirus.

22. The method of claim 21, wherein the feline coronavirus is feline infectious peritonitis.

23. The method of claim 20, wherein the coronavirus is a human coronavirus.

24. The method of claim 23, wherein the human coronavirus is selected from Severe Acute Respiratory Syndrome coronavirus 2 (SARS-CoV-2), Severe Acute Respiratory syndrome coronavirus 1 (SARS-CoV-1) and Middle Eastern Respiratory syndrome-related coronavirus (MERS-CoV).

* * * * *